(12) United States Patent
Tamarkin et al.

(10) Patent No.: US 8,435,498 B2
(45) Date of Patent: *May 7, 2013

(54) PENETRATING PHARMACEUTICAL FOAM

(75) Inventors: Dov Tamarkin, Maccabim (IL); Doron Friedman, Karmei Yosef (IL); Meir Eini, Ness Ziona (IL)

(73) Assignee: Foamix Ltd., Rehovot (IL)

( * ) Notice: Subject to any disclaimer, the term of this patent is extended or adjusted under 35 U.S.C. 154(b) by 93 days.

This patent is subject to a terminal disclaimer.

(21) Appl. No.: 12/752,718

(22) Filed: Apr. 1, 2010

(65) Prior Publication Data

US 2010/0284938 A1    Nov. 11, 2010

Related U.S. Application Data

(60) Division of application No. 10/922,358, filed on Aug. 20, 2004, now Pat. No. 7,700,076, and a continuation-in-part of application No. PCT/IB03/05527, filed on Oct. 24, 2002, said application No. 10/922,358 is a continuation-in-part of application No. 10/911,367, filed on Aug. 4, 2004.

(60) Provisional application No. 60/497,648, filed on Aug. 25, 2003, provisional application No. 60/429,546, filed on Nov. 29, 2002, provisional application No. 60/492,385, filed on Aug. 4, 2003.

(30) Foreign Application Priority Data

Oct. 25, 2002    (IL) .......................................... 152486

(51) Int. Cl.
A61K 9/12     (2006.01)
A61K 9/00     (2006.01)
A61K 8/02     (2006.01)
A61K 31/19    (2006.01)
A61K 31/17    (2006.01)

(52) U.S. Cl.
USPC ............... 424/47; 424/43; 424/401; 514/945; 514/588; 514/557

(58) Field of Classification Search ............ 424/47, 424/43, 401; 514/945, 588, 557
See application file for complete search history.

(56) References Cited

U.S. PATENT DOCUMENTS

| | | | |
|---|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |

(Continued)

FOREIGN PATENT DOCUMENTS

| AU | 198780257 | 9/1986 |
|---|---|---|
| CA | 2422244 | 9/2003 |

(Continued)

OTHER PUBLICATIONS

U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
Barry, B.W. et al, Comparative bio-availability and activity of proprietary topical corticosteroid preparations: vasoconstrictor assays on thirty-one ointments, British Journal of Dermatology, 93, 563-571, 1975.
Benet, et al., Application of NMR for the Determination of HLB Values of Nonionic Surfactants, Journal of the American Oil Chemists Society, vol. 49, 1972, 499-500.

(Continued)

*Primary Examiner* — Abigal Fisher
(74) *Attorney, Agent, or Firm* — Fish & Richardson P.C.

(57) ABSTRACT

The invention relates to an alcohol-free cosmetic or pharmaceutical foam composition comprising water, a hydrophobic solvent, a surface-active agent, a gelling agent, an active component selected from the group of urea, hydroxy acid and a therapeutic enhancer and a propellant. The foam further comprises active agents and excipients with therapeutic properties having enhanced skin penetration.

24 Claims, No Drawings

U.S. PATENT DOCUMENTS

| | | | |
|---|---|---|---|
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |

| | | | | | |
|---|---|---|---|---|---|
| 5,094,853 A | 3/1992 | Hagarty | 5,597,560 A | 1/1997 | Bergamini et al. |
| 5,100,917 A | 3/1992 | Flynn et al. | 5,603,940 A | 2/1997 | Candau et al. |
| 5,104,645 A | 4/1992 | Cardin et al. | 5,605,679 A | 2/1997 | Hansenne et al. |
| 5,112,359 A | 5/1992 | Murphy et al. | 5,608,119 A | 3/1997 | Amano et al. |
| 5,114,718 A | 5/1992 | Damani | 5,611,463 A | 3/1997 | Favre |
| 5,122,519 A | 6/1992 | Ritter | 5,612,056 A | 3/1997 | Jenner et al. |
| 5,130,121 A | 7/1992 | Kopolow et al. | 5,613,583 A | 3/1997 | Kono et al. |
| 5,133,972 A | 7/1992 | Ferrini et al. | 5,613,623 A | 3/1997 | Hildebrandt |
| 5,135,915 A | 8/1992 | Czarniecki et al. | 5,614,171 A | 3/1997 | Clavenna et al. |
| 5,137,714 A | 8/1992 | Scott | 5,614,178 A | 3/1997 | Bloom et al. |
| 5,143,717 A | 9/1992 | Davis | 5,635,469 A | 6/1997 | Fowler et al. |
| 5,156,765 A | 10/1992 | Smrt | 5,641,480 A | 6/1997 | Vermeer |
| 5,164,357 A | 11/1992 | Bartman et al. | 5,643,600 A | 7/1997 | Mathur |
| 5,164,367 A | 11/1992 | Pickart | 5,645,842 A | 7/1997 | Gruning et al. |
| 5,167,950 A | 12/1992 | Lins | 5,650,554 A | 7/1997 | Moloney |
| 5,171,577 A | 12/1992 | Griat et al. | 5,658,575 A | 8/1997 | Ribier et al. |
| 5,196,405 A | 3/1993 | Packman | 5,658,749 A | 8/1997 | Thornton |
| 5,204,093 A | 4/1993 | Victor | 5,658,956 A | 8/1997 | Martin et al. |
| 5,208,031 A | 5/1993 | Kelly | 5,663,208 A | 9/1997 | Martin |
| 5,217,707 A | 6/1993 | Szabo et al. | 5,672,634 A | 9/1997 | Tseng et al. |
| 5,219,877 A | 6/1993 | Shah et al. | 5,679,324 A * | 10/1997 | Lisboa et al. .................. 424/45 |
| 5,221,696 A | 6/1993 | Ke et al. | 5,683,710 A | 11/1997 | Akemi et al. |
| 5,230,897 A | 7/1993 | Griffin et al. | 5,686,088 A | 11/1997 | Mitra et al. |
| 5,236,707 A | 8/1993 | Stewart, II | 5,693,258 A | 12/1997 | Tonomura et al. |
| 5,252,246 A | 10/1993 | Ding et al. | 5,695,551 A | 12/1997 | Buckingham et al. |
| 5,254,334 A | 10/1993 | Ramirez et al. | 5,700,396 A | 12/1997 | Suzuki et al. |
| 5,262,407 A | 11/1993 | Leveque et al. | 5,716,611 A | 2/1998 | Oshlack et al. |
| 5,266,592 A | 11/1993 | Grub et al. | 5,716,621 A | 2/1998 | Bello |
| 5,279,819 A | 1/1994 | Hayes | 5,719,122 A | 2/1998 | Chiodini et al. |
| 5,286,475 A | 2/1994 | Louvet et al. | 5,719,197 A | 2/1998 | Kanios et al. |
| 5,300,286 A | 4/1994 | Gee | 5,725,872 A | 3/1998 | Stamm et al. |
| 5,301,841 A | 4/1994 | Fuchs | 5,725,874 A | 3/1998 | Oda |
| 5,308,643 A | 5/1994 | Osipow et al. | 5,730,964 A | 3/1998 | Waldstreicher |
| 5,314,904 A | 5/1994 | Egidio et al. | 5,733,558 A | 3/1998 | Breton et al. |
| 5,322,683 A | 6/1994 | Mackles et al. | 5,733,572 A | 3/1998 | Unger et al. |
| 5,326,557 A | 7/1994 | Glover et al. | 5,747,049 A | 5/1998 | Tominaga |
| 5,344,051 A | 9/1994 | Brown | 5,753,241 A | 5/1998 | Ribier et al. |
| 5,346,135 A | 9/1994 | Vincent | 5,753,245 A | 5/1998 | Fowler et al. |
| 5,352,437 A | 10/1994 | Nakagawa et al. | 5,759,520 A | 6/1998 | Sachetto |
| 5,369,131 A | 11/1994 | Poli et al. | 5,759,579 A | 6/1998 | Singh et al. |
| 5,378,451 A | 1/1995 | Gorman et al. | 5,767,104 A | 6/1998 | Bar-Shalom et al. |
| 5,378,730 A | 1/1995 | Lee et al. | 5,773,410 A | 6/1998 | Yamamoto |
| 5,380,761 A | 1/1995 | Szabo Anna Z. et al. | 5,783,202 A | 7/1998 | Tomlinson et al. |
| 5,384,308 A | 1/1995 | Henkin | 5,788,664 A | 8/1998 | Scalise |
| 5,385,943 A | 1/1995 | Nazzaro-Porro | 5,792,448 A | 8/1998 | Dubief et al. |
| 5,389,676 A | 2/1995 | Michaels | 5,792,922 A | 8/1998 | Moloney et al. |
| 5,397,312 A | 3/1995 | Rademaker et al. | 5,797,955 A | 8/1998 | Walters |
| 5,398,846 A | 3/1995 | Corba et al. | 5,804,546 A | 9/1998 | Hall et al. |
| 5,399,205 A | 3/1995 | Shinohara et al. | 5,817,322 A | 10/1998 | Xu et al. |
| 5,411,992 A | 5/1995 | Eini et al. | 5,824,650 A | 10/1998 | De Lacharriere et al. |
| 5,422,361 A | 6/1995 | Munayyer et al. | 5,833,960 A | 11/1998 | Gers-Barlag et al. |
| 5,429,815 A | 7/1995 | Faryniarz et al. | 5,833,961 A | 11/1998 | Siegfried et al. |
| 5,435,996 A | 7/1995 | Glover et al. | 5,837,270 A | 11/1998 | Burgess |
| 5,447,725 A | 9/1995 | Damani et al. | 5,840,744 A | 11/1998 | Borgman |
| 5,449,520 A | 9/1995 | Frigerio et al. | 5,840,771 A | 11/1998 | Oldham et al. |
| 5,451,404 A | 9/1995 | Furman | 5,843,411 A | 12/1998 | Hernandez et al. |
| 5,482,965 A | 1/1996 | Rajadhyaksha | 5,846,983 A | 12/1998 | Sandborn et al. |
| 5,491,245 A | 2/1996 | Gruning et al. | 5,849,042 A | 12/1998 | Lim et al. |
| 5,500,211 A | 3/1996 | George et al. | 5,856,452 A | 1/1999 | Moloney et al. |
| 5,508,033 A | 4/1996 | Briand et al. | 5,858,371 A | 1/1999 | Singh et al. |
| 5,512,555 A | 4/1996 | Waldstreicher | 5,865,347 A | 2/1999 | Welschoff |
| 5,514,367 A | 5/1996 | Lentini et al. | 5,866,040 A | 2/1999 | Nakama et al. |
| 5,514,369 A | 5/1996 | Salka et al. | 5,869,529 A | 2/1999 | Sintov et al. |
| 5,520,918 A | 5/1996 | Smith | 5,871,720 A | 2/1999 | Gutierrez et al. |
| 5,523,078 A | 6/1996 | Baylin | 5,877,216 A | 3/1999 | Place et al. |
| 5,527,534 A | 6/1996 | Myhling | 5,879,469 A | 3/1999 | Avram et al. |
| 5,527,822 A | 6/1996 | Scheiner | 5,881,493 A | 3/1999 | Restive |
| 5,529,770 A | 6/1996 | McKinzie et al. | 5,885,581 A | 3/1999 | Massand |
| 5,531,703 A | 7/1996 | Skwarek et al. | 5,889,028 A | 3/1999 | Sandborn et al. |
| 5,534,261 A | 7/1996 | Rodgers et al. | 5,889,054 A | 3/1999 | Yu et al. |
| 5,536,743 A | 7/1996 | Borgman | 5,891,458 A | 4/1999 | Britton et al. |
| 5,540,853 A | 7/1996 | Trinh et al. | 5,902,574 A | 5/1999 | Stoner et al. |
| 5,545,401 A | 8/1996 | Shanbrom | 5,902,789 A | 5/1999 | Stoltz |
| 5,567,420 A | 10/1996 | McEleney et al. | 5,905,092 A | 5/1999 | Osborne et al. |
| 5,576,016 A | 11/1996 | Amselem et al. | 5,910,382 A | 6/1999 | Goodenough et al. |
| 5,578,315 A | 11/1996 | Chien et al. | 5,911,981 A | 6/1999 | Dahms et al. |
| 5,585,104 A | 12/1996 | Ha et al. | 5,912,007 A | 6/1999 | Pan et al. |
| 5,589,157 A | 12/1996 | Hatfield | 5,914,122 A | 6/1999 | Otterbeck et al. |
| 5,589,515 A | 12/1996 | Suzuki et al. | 5,914,310 A | 6/1999 | Li et al. |

| | | | | | | |
|---|---|---|---|---|---|---|
| 5,922,331 | A | 7/1999 | Mausner | 6,341,717 | B2 | 1/2002 | Auer |
| 5,925,669 | A | 7/1999 | Katz et al. | 6,344,218 | B1 | 2/2002 | Dodd et al. |
| 5,948,682 | A | 9/1999 | Moloney | 6,348,229 | B1 | 2/2002 | Eini et al. |
| 5,951,544 | A | 9/1999 | Konwitz | 6,358,541 | B1 | 3/2002 | Goodman |
| 5,951,989 | A | 9/1999 | Heymann | 6,364,854 | B1 | 4/2002 | Ferrer et al. |
| 5,951,993 | A | 9/1999 | Scholz et al. | 6,372,234 | B1 | 4/2002 | Deckers et al. |
| 5,952,373 | A | 9/1999 | Lanzendorfer et al. | 6,375,960 | B1 | 4/2002 | Simonnet et al. |
| 5,952,392 | A | 9/1999 | Katz et al. | 6,383,471 | B1 | 5/2002 | Chen et al. |
| 5,955,414 | A | 9/1999 | Brown et al. | 6,395,258 | B1 | 5/2002 | Steer |
| 5,959,161 | A | 9/1999 | Kenmochi et al. | 6,395,300 | B1 | 5/2002 | Straub et al. |
| 5,961,957 | A | 10/1999 | McAnalley | 6,403,061 | B1 | 6/2002 | Candau et al. |
| 5,961,998 | A | 10/1999 | Arnaud et al. | 6,403,069 | B1 | 6/2002 | Chopra et al. |
| 5,972,310 | A | 10/1999 | Sachetto | 6,410,036 | B1 | 6/2002 | De Rosa et al. |
| 5,976,555 | A | 11/1999 | Liu et al. | 6,423,323 | B2 | 7/2002 | Neubourg |
| 5,980,904 | A | 11/1999 | Leverett et al. | 6,428,772 | B1 | 8/2002 | Singh et al. |
| 5,990,100 | A | 11/1999 | Rosenberg et al. | 6,433,003 | B1 | 8/2002 | Bobrove et al. |
| 5,993,846 | A | 11/1999 | Friedman et al. | 6,433,024 | B1 | 8/2002 | Popp et al. |
| 6,001,341 | A | 12/1999 | Genova et al. | 6,433,033 | B1 | 8/2002 | Isobe et al. |
| 6,006,948 | A | 12/1999 | Auer | 6,437,006 | B1 | 8/2002 | Yoon et al. |
| 6,019,967 | A | 2/2000 | Breton et al. | 6,440,429 | B1 | 8/2002 | Torizuka et al. |
| 6,024,942 | A | 2/2000 | Tanner et al. | 6,447,801 | B1 | 9/2002 | Salafsky et al. |
| 6,030,630 | A | 2/2000 | Fleury et al. | 6,455,076 | B1 | 9/2002 | Hahn et al. |
| 6,033,647 | A | 3/2000 | Touzan et al. | 6,468,989 | B1 | 10/2002 | Chang et al. |
| 6,039,936 | A | 3/2000 | Restle et al. | 6,479,058 | B1 | 11/2002 | McCadden |
| 6,042,848 | A | 3/2000 | Lawyer et al. | 6,486,168 | B1 | 11/2002 | Skwierczynski et al. |
| 6,045,779 | A | 4/2000 | Mueller et al. | 6,488,947 | B1 | 12/2002 | Bekele |
| 6,071,536 | A | 6/2000 | Suzuki et al. | 6,511,655 | B1 | 1/2003 | Muller et al. |
| 6,075,056 | A | 6/2000 | Quigley, Jr. et al. | 6,514,487 | B1 | 2/2003 | Barr |
| 6,080,394 | A | 6/2000 | Lin et al. | 6,524,594 | B1 | 2/2003 | Santora et al. |
| 6,087,317 | A | 7/2000 | Gee | 6,531,118 | B1 | 3/2003 | Gonzalez et al. |
| 6,090,772 | A | 7/2000 | Kaiser et al. | 6,534,455 | B1 | 3/2003 | Maurin et al. |
| 6,093,408 | A | 7/2000 | Hasenoehrl et al. | 6,536,629 | B2 | 3/2003 | van der Heijden |
| 6,096,756 | A | 8/2000 | Crain et al. | 6,544,530 | B1 | 4/2003 | Friedman |
| 6,110,477 | A | 8/2000 | Hernandez et al. | 6,544,562 | B1 | 4/2003 | Singh et al. |
| 6,110,966 | A | 8/2000 | Pollock | 6,547,063 | B1 | 4/2003 | Zaveri et al. |
| 6,113,888 | A | 9/2000 | Castro et al. | 6,548,074 | B1 | 4/2003 | Mohammadi |
| 6,116,466 | A | 9/2000 | Gueret | 6,562,355 | B1 | 5/2003 | Renault |
| 6,121,210 | A | 9/2000 | Taylor | 6,566,350 | B2 | 5/2003 | Ono et al. |
| 6,126,920 | A | 10/2000 | Jones et al. | 6,582,679 | B2 | 6/2003 | Stein et al. |
| 6,140,355 | A | 10/2000 | Egidio et al. | 6,582,710 | B2 | 6/2003 | Deckers et al. |
| 6,146,645 | A | 11/2000 | Deckers et al. | 6,589,509 | B2 | 7/2003 | Keller et al. |
| 6,146,664 | A | 11/2000 | Siddiqui | 6,596,287 | B2 | 7/2003 | Deckers et al. |
| 6,162,834 | A | 12/2000 | Sebillotte-Arnaud et al. | 6,599,513 | B2 | 7/2003 | Deckers et al. |
| 6,165,455 | A | 12/2000 | Torgerson et al. | 6,620,773 | B1 | 9/2003 | Stork et al. |
| 6,168,576 | B1 | 1/2001 | Reynolds | 6,638,981 | B2 | 10/2003 | Williams et al. |
| 6,171,347 | B1 | 1/2001 | Kunz et al. | 6,649,571 | B1 | 11/2003 | Morgan |
| 6,180,669 | B1 | 1/2001 | Tamarkin | 6,649,574 | B2 | 11/2003 | Cardis et al. |
| 6,183,762 | B1 | 2/2001 | Deckers et al. | 6,672,483 | B1 | 1/2004 | Roy |
| 6,186,367 | B1 | 2/2001 | Harrold | 6,682,726 | B2 | 1/2004 | Marchesi et al. |
| 6,187,290 | B1 | 2/2001 | Gilchrist et al. | 6,691,898 | B2 | 2/2004 | Hurray et al. |
| 6,189,810 | B1 | 2/2001 | Nerushai et al. | 6,709,663 | B2 | 3/2004 | Espinoza |
| 6,190,365 | B1 | 2/2001 | Abbott et al. | 6,723,309 | B1 | 4/2004 | Deane |
| 6,204,285 | B1 | 3/2001 | Fabiano et al. | 6,730,288 | B1 | 5/2004 | Abram |
| 6,210,656 | B1 | 4/2001 | Touzan et al. | 6,753,000 | B2 | 6/2004 | Breton et al. |
| 6,210,742 | B1 | 4/2001 | Deckers et al. | 6,753,167 | B2 | 6/2004 | Moloney et al. |
| 6,214,318 | B1 | 4/2001 | Osipow et al. | 6,762,158 | B2 | 7/2004 | Lukenbach et al. |
| 6,214,788 | B1 | 4/2001 | Velazco et al. | 6,765,001 | B2 | 7/2004 | Gans et al. |
| 6,221,381 | B1 | 4/2001 | Shelford et al. | 6,774,114 | B2 | 8/2004 | Castiel et al. |
| 6,221,823 | B1 | 4/2001 | Crisanti et al. | 6,777,591 | B1 | 8/2004 | Chaudhary et al. |
| 6,224,888 | B1 | 5/2001 | Vatter et al. | 6,790,435 | B1 | 9/2004 | Ma et al. |
| 6,231,837 | B1 | 5/2001 | Stroud et al. | 6,796,973 | B1 | 9/2004 | Contente et al. |
| 6,232,315 | B1 | 5/2001 | Shafer et al. | RE38,623 | E | 10/2004 | Hernandez et al. |
| 6,251,369 | B1 | 6/2001 | Stoltz | 6,811,767 | B1 | 11/2004 | Bosch et al. |
| 6,258,374 | B1 | 7/2001 | Friess et al. | 6,834,778 | B2 | 12/2004 | Jinbo et al. |
| 6,271,295 | B1 | 8/2001 | Powell et al. | 6,843,390 | B1 | 1/2005 | Bristor |
| 6,274,150 | B1 | 8/2001 | Simonnet et al. | 6,875,438 | B2 | 4/2005 | Kraemer et al. |
| 6,287,546 | B1 | 9/2001 | Reich et al. | 6,881,271 | B2 | 4/2005 | Ochiai |
| 6,294,550 | B1 | 9/2001 | Place et al. | 6,890,567 | B2 | 5/2005 | Nakatsu et al. |
| 6,299,023 | B1 | 10/2001 | Arnone | 6,902,737 | B2 | 6/2005 | Quemin et al. |
| 6,299,032 | B1 | 10/2001 | Hamilton | 6,911,211 | B2 | 6/2005 | Eini et al. |
| 6,299,900 | B1 | 10/2001 | Reed et al. | 6,946,120 | B2 | 9/2005 | Wai-Chiu So et al. |
| 6,305,578 | B1 | 10/2001 | Hildebrandt et al. | 6,946,139 | B2 | 9/2005 | Henning |
| 6,306,841 | B1 | 10/2001 | Place et al. | 6,951,654 | B2 | 10/2005 | Malcolm et al. |
| 6,308,863 | B1 | 10/2001 | Harman | 6,955,816 | B2 | 10/2005 | Klysz |
| 6,319,913 | B1 | 11/2001 | Mak et al. | 6,956,062 | B2 | 10/2005 | Beilfuss et al. |
| 6,328,950 | B1 | 12/2001 | Franzke et al. | 6,958,154 | B2 | 10/2005 | Andolino Brandt et al. |
| 6,328,982 | B1 | 12/2001 | Shiroyama et al. | 6,967,012 | B2 | 11/2005 | Meisner et al. |
| 6,333,362 | B1 | 12/2001 | Lorant | 6,967,023 | B1 | 11/2005 | Eini et al. |
| 6,335,022 | B1 | 1/2002 | Simonnet et al. | 6,968,982 | B1 | 11/2005 | Burns |

| | | |
|---|---|---|
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |
| 7,645,803 B2 * | 1/2010 | Tamarkin et al. ............... 424/43 |
| 7,654,415 B2 | 2/2010 | van der Heijden |
| 7,682,523 B2 | 3/2010 | Weisman et al. |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,820,145 B2 | 10/2010 | Tamarkin et al. |
| 7,960,416 B2 | 6/2011 | Sato et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 * | 12/2005 | Friedman et al. ............... 424/45 |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |

| | | | |
|---|---|---|---|
| 2006/0110418 A1 | 5/2006 | Johnson | |
| 2006/0114745 A1 | 6/2006 | Ollmann et al. | |
| 2006/0121073 A1 | 6/2006 | Goyal et al. | |
| 2006/0140984 A1 | 6/2006 | Tamarkin et al. | |
| 2006/0140990 A1 | 6/2006 | Bortz et al. | |
| 2006/0160713 A1 | 7/2006 | Sekine et al. | |
| 2006/0165616 A1 | 7/2006 | Brock et al. | |
| 2006/0177392 A1 | 8/2006 | Walden | |
| 2006/0193789 A1 | 8/2006 | Tamarkin et al. | |
| 2006/0193813 A1 | 8/2006 | Simonnet | |
| 2006/0204446 A1 | 9/2006 | Lulla et al. | |
| 2006/0222675 A1 | 10/2006 | Sabnis et al. | |
| 2006/0233721 A1 | 10/2006 | Tamarkin et al. | |
| 2006/0239937 A2 | 10/2006 | Neubourg | |
| 2006/0251684 A1 | 11/2006 | Annis et al. | |
| 2006/0254597 A1 | 11/2006 | Thompson | |
| 2006/0263323 A1 | 11/2006 | Hoang et al. | |
| 2006/0269485 A1 | 11/2006 | Friedman et al. | |
| 2006/0272199 A1 | 12/2006 | Licciardello et al. | |
| 2006/0275218 A1 | 12/2006 | Tamarkin et al. | |
| 2006/0275221 A1* | 12/2006 | Tamarkin et al. | 424/47 |
| 2006/0285912 A1 | 12/2006 | Eini et al. | |
| 2006/0292080 A1 | 12/2006 | Abram et al. | |
| 2007/0009607 A1 | 1/2007 | Jones | |
| 2007/0017696 A1 | 1/2007 | Lin et al. | |
| 2007/0020213 A1 | 1/2007 | Tamarkin et al. | |
| 2007/0020304 A1 | 1/2007 | Tamarkin et al. | |
| 2007/0027055 A1 | 2/2007 | Koivisto et al. | |
| 2007/0036831 A1 | 2/2007 | Baker | |
| 2007/0059253 A1 | 3/2007 | Popp et al. | |
| 2007/0069046 A1 | 3/2007 | Eini et al. | |
| 2007/0071688 A1 | 3/2007 | Illel et al. | |
| 2007/0098647 A1 | 5/2007 | Neubourg | |
| 2007/0134174 A1 | 6/2007 | Irwin et al. | |
| 2007/0140999 A1 | 6/2007 | Puglia et al. | |
| 2007/0142263 A1 | 6/2007 | Stahl et al. | |
| 2007/0148112 A1 | 6/2007 | Dingley et al. | |
| 2007/0148194 A1 | 6/2007 | Amiji et al. | |
| 2007/0154402 A1 | 7/2007 | Trumbore et al. | |
| 2007/0160548 A1 | 7/2007 | Riccardi et al. | |
| 2007/0237724 A1 | 10/2007 | Abram et al. | |
| 2007/0253911 A1 | 11/2007 | Tamarkin et al. | |
| 2007/0264317 A1 | 11/2007 | Yosha et al. | |
| 2007/0271235 A1 | 11/2007 | Frank et al. | |
| 2007/0280891 A1 | 12/2007 | Tamarkin et al. | |
| 2007/0281999 A1 | 12/2007 | Fox et al. | |
| 2007/0292355 A1* | 12/2007 | Tamarkin et al. | 424/43 |
| 2007/0292359 A1 | 12/2007 | Friedman et al. | |
| 2007/0292461 A1 | 12/2007 | Tamarkin et al. | |
| 2008/0008397 A1 | 1/2008 | Kisilev | |
| 2008/0015263 A1 | 1/2008 | Bolotin et al. | |
| 2008/0015271 A1 | 1/2008 | Abram et al. | |
| 2008/0031907 A1 | 2/2008 | Tamarkin et al. | |
| 2008/0031908 A1 | 2/2008 | Aubrun-Sonneville et al. | |
| 2008/0035155 A1 | 2/2008 | Dahl | |
| 2008/0044444 A1 | 2/2008 | Tamarkin et al. | |
| 2008/0058055 A1 | 3/2008 | LeMay et al. | |
| 2008/0063682 A1 | 3/2008 | Cashman et al. | |
| 2008/0069779 A1 | 3/2008 | Tamarkin et al. | |
| 2008/0131378 A1 | 6/2008 | Keller et al. | |
| 2008/0138293 A1 | 6/2008 | Tamarkin et al. | |
| 2008/0138296 A1 | 6/2008 | Tamarkin et al. | |
| 2008/0152596 A1 | 6/2008 | Friedman et al. | |
| 2008/0153789 A1 | 6/2008 | Dmowski et al. | |
| 2008/0166303 A1 | 7/2008 | Tamarkin et al. | |
| 2008/0167376 A1 | 7/2008 | Bar-Or et al. | |
| 2008/0181854 A1 | 7/2008 | Eini et al. | |
| 2008/0188445 A1 | 8/2008 | Muldoon et al. | |
| 2008/0188446 A1 | 8/2008 | Muldoon et al. | |
| 2008/0193762 A1 | 8/2008 | Dubertret et al. | |
| 2008/0206155 A1* | 8/2008 | Tamarkin et al. | 424/44 |
| 2008/0206159 A1 | 8/2008 | Tamarkin et al. | |
| 2008/0206161 A1* | 8/2008 | Tamarkin et al. | 424/45 |
| 2008/0241079 A1 | 10/2008 | Neubourg | |
| 2008/0253973 A1 | 10/2008 | Tamarkin et al. | |
| 2008/0255498 A1 | 10/2008 | Houle | |
| 2008/0260655 A1 | 10/2008 | Tamarkin et al. | |
| 2008/0292560 A1 | 11/2008 | Tamarkin et al. | |
| 2008/0299220 A1 | 12/2008 | Tamarkin et al. | |
| 2008/0311167 A1 | 12/2008 | Oronsky et al. | |
| 2008/0317679 A1 | 12/2008 | Tamarkin et al. | |
| 2009/0041680 A1 | 2/2009 | Tamarkin et al. | |
| 2009/0068118 A1 | 3/2009 | Eini et al. | |
| 2009/0093514 A1 | 4/2009 | Statham et al. | |
| 2009/0130029 A1 | 5/2009 | Tamarkin et al. | |
| 2009/0131488 A1 | 5/2009 | Harel et al. | |
| 2009/0175799 A1 | 7/2009 | Tamarkin et al. | |
| 2009/0180970 A1 | 7/2009 | Tamarkin et al. | |
| 2009/0291917 A1 | 11/2009 | Akama et al. | |
| 2009/0317338 A1 | 12/2009 | Tamarkin et al. | |
| 2010/0111879 A1* | 5/2010 | Tamarkin et al. | 424/45 |
| 2010/0221194 A1 | 9/2010 | Loupenok | |
| 2011/0002857 A1* | 1/2011 | Tamarkin et al. | 424/47 |
| 2011/0002969 A1 | 1/2011 | Serraima et al. | |
| 2011/0212033 A1 | 9/2011 | Tamarkin et al. | |
| 2011/0268665 A1 | 11/2011 | Tamarkin et al. | |

FOREIGN PATENT DOCUMENTS

| | | |
|---|---|---|
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0 156 507 | 10/1985 |
| EP | 0 186 453 | 7/1986 |
| EP | 0 211 550 | 2/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 670 698 | 6/2006 |
| EP | 1 734 927 | 12/2006 |
| EP | 1 758 547 | 3/2007 |
| EP | 1 584 324 | 11/2007 |
| EP | 1 889 609 | 2/2008 |
| FR | 2 591 331 | 6/1987 |
| FR | 2 640 942 | 6/1990 |

| | | | | | | |
|---|---|---|---|---|---|---|
| FR | 2 736 824 | 1/1997 | | JP | 11250543 | 9/1999 |
| FR | 2 774 595 | 8/1999 | | JP | 2000/017174 | 1/2000 |
| FR | 2 789 371 | 8/2000 | | JP | 2000/080017 | 3/2000 |
| FR | 2 793 479 | 11/2000 | | JP | 2000/128734 | 5/2000 |
| FR | 2 814 959 | 4/2002 | | JP | 2000/191429 | 7/2000 |
| FR | 2 833 246 | 6/2003 | | JP | 2000/239140 | 9/2000 |
| FR | 2 840 903 | 12/2003 | | JP | 2000/351726 | 12/2000 |
| FR | 2 843 373 | 2/2004 | | JP | 2000/354623 | 12/2000 |
| FR | 2 845 672 | 4/2004 | | JP | 2001/002526 | 1/2001 |
| FR | 2 848 998 | 6/2004 | | JP | 2001/019606 | 1/2001 |
| FR | 2 860 976 | 4/2005 | | JP | 2001/072963 | 3/2001 |
| FR | 2 915 891 | 11/2008 | | JP | 2002/012513 | 1/2002 |
| GB | 808 104 | 1/1959 | | JP | 2002/047136 | 2/2002 |
| GB | 808 105 | 1/1959 | | JP | 2002/524490 | 8/2002 |
| GB | 922 930 | 4/1963 | | JP | 2002/302419 | 10/2002 |
| GB | 933 486 | 8/1963 | | JP | 2003/012511 | 1/2003 |
| GB | 998 490 | 7/1965 | | JP | 2003/055146 | 2/2003 |
| GB | 1 026 831 | 4/1966 | | JP | 2004/047136 | 2/2004 |
| GB | 1 033 299 | 6/1966 | | JP | 2004/250435 | 9/2004 |
| GB | 1 081 949 | 9/1967 | | JP | 2004/348277 | 12/2004 |
| GB | 1 121 358 | 7/1968 | | JP | 2005/314323 | 11/2005 |
| GB | 1 162 684 | 8/1969 | | JP | 2005/350378 | 12/2005 |
| GB | 1 170 152 | 11/1969 | | JP | 2006/008574 | 1/2006 |
| GB | 1 201 918 | 8/1970 | | JP | 2006/036317 | 2/2006 |
| GB | 1 347 950 | 2/1974 | | JP | 2006/103799 | 4/2006 |
| GB | 1 351 761 | 5/1974 | | JP | 2006525145 | 11/2006 |
| GB | 1 351 762 | 5/1974 | | JP | 2007/131539 | 5/2007 |
| GB | 1 353 381 | 5/1974 | | JP | S48-92282 | 12/2007 |
| GB | 1 376 649 | 12/1974 | | KR | 143232 | 7/1998 |
| GB | 1 397 285 | 6/1975 | | KR | 2001/003063 | 1/2001 |
| GB | 1 408 036 | 10/1975 | | UA | 66796 | 6/2004 |
| GB | 1 457 671 | 12/1976 | | WO | 82/01821 | 6/1982 |
| GB | 1 489 672 | 10/1977 | | WO | 86/05389 | 9/1986 |
| GB | 2 004 746 | 4/1979 | | WO | 88/01502 | 3/1988 |
| GB | 1 561 423 | 2/1980 | | WO | 88/01863 | 3/1988 |
| GB | 2 114 580 | 8/1983 | | WO | 88/08316 | 11/1988 |
| GB | 2 153 686 | 8/1985 | | WO | 89/06537 | 7/1989 |
| GB | 2 172 298 | 9/1986 | | WO | 90/05774 | 5/1990 |
| GB | 2 206 099 | 12/1988 | | WO | 91/11991 | 8/1991 |
| GB | 2 166 651 | 5/1996 | | WO | 92/00077 | 1/1992 |
| GB | 2 337 461 | 11/1999 | | WO | 92/05142 | 4/1992 |
| GB | 2 367 809 | 4/2002 | | WO | 92/05763 | 4/1992 |
| GB | 2 406 330 | 3/2005 | | WO | 92/11839 | 7/1992 |
| GB | 2 406 791 | 4/2005 | | WO | 93/25189 | 12/1993 |
| IL | 49491 | 9/1979 | | WO | 94/06440 | 3/1994 |
| IL | 152 486 | 5/2003 | | WO | 96/03115 | 2/1996 |
| JP | 60001113 | 4/1978 | | WO | 96/19921 | 7/1996 |
| JP | 55069682 | 5/1980 | | WO | 96/24325 | 8/1996 |
| JP | 57044429 | 3/1982 | | WO | 96/26711 | 9/1996 |
| JP | 56039815 | 4/1984 | | WO | 96/27376 | 9/1996 |
| JP | 61275395 | 12/1986 | | WO | 96/39119 | 12/1996 |
| JP | 62241701 | 10/1987 | | WO | 97/03638 | 2/1997 |
| JP | 6357511 | 3/1988 | | WO | 97/39745 | 10/1997 |
| JP | 63119420 | 5/1988 | | WO | 98/017282 | 4/1998 |
| JP | 1100111 | 4/1989 | | WO | 98/18472 | 5/1998 |
| JP | 1156906 | 6/1989 | | WO | 98/19654 | 5/1998 |
| JP | 2184614 | 7/1990 | | WO | 98/21955 | 5/1998 |
| JP | 2255890 | 10/1990 | | WO | 98/23291 | 6/1998 |
| JP | 4282311 | 10/1992 | | WO | 98/36733 | 8/1998 |
| JP | 4312521 | 11/1992 | | WO | 98/52536 | 11/1998 |
| JP | 5070340 | 3/1993 | | WO | 99/08649 | 2/1999 |
| JP | 5213734 | 8/1993 | | WO | 99/20250 | 4/1999 |
| JP | 6100414 | 4/1994 | | WO | 99/37282 | 7/1999 |
| JP | H06-263630 | 6/1994 | | WO | 99/53923 | 10/1999 |
| JP | 6329532 | 11/1994 | | WO | 00/09082 | 2/2000 |
| JP | 2007/155667 | 6/1995 | | WO | 00/15193 | 3/2000 |
| JP | 7215835 | 8/1995 | | WO | 00/23051 | 4/2000 |
| JP | 2008/040899 | 2/1996 | | WO | 00/33825 | 6/2000 |
| JP | 8501529 | 2/1996 | | WO | 00/38731 | 7/2000 |
| JP | 8119831 | 5/1996 | | WO | 00/61076 | 10/2000 |
| JP | 8165218 | 6/1996 | | WO | 00/76461 | 12/2000 |
| JP | 8277209 | 10/1996 | | WO | 01/05366 | 1/2001 |
| JP | 09 084855 | 3/1997 | | WO | 01/08681 | 2/2001 |
| JP | 9099553 | 4/1997 | | WO | 01/10961 | 2/2001 |
| JP | 9110636 | 4/1997 | | WO | 01/53198 | 7/2001 |
| JP | 10114619 | 5/1998 | | WO | 01/54212 | 7/2001 |
| JP | 3050289 | 9/1998 | | WO | 01/54679 | 8/2001 |
| JP | 2010/332456 | 12/1998 | | WO | 01/62209 | 8/2001 |
| JP | 11501045 | 1/1999 | | WO | 01/70242 | 9/2001 |

| | | |
|---|---|---|
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | 02/00820 | 1/2002 |
| WO | 02/15860 | 2/2002 |
| WO | 02/15873 | 2/2002 |
| WO | 02/28435 | 4/2002 |
| WO | 02/41847 | 5/2002 |
| WO | 02/43490 | 6/2002 |
| WO | 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | 2007/012977 | 2/2007 |
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | 2007/085899 | 8/2007 |
| WO | 2007/085902 | 8/2007 |
| WO | 2007/099396 | 9/2007 |
| WO | 2007/111962 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | 2009/098595 | 8/2009 |
| WO | 2011/039637 | 4/2011 |
| WO | 2011/039638 | 4/2011 |

OTHER PUBLICATIONS

927 Carbowax 1000MSDS; http://www.sciencelab.com/xMSDS-Polyethylene.sub.--glycol.sub.--1000-9926-622. Accessed Dec. 13, 2008, 6 pages.

Cheshire, et al., Disorders of Sweating, www.medscape.com, Semin Neurol 23(4):399-406, 2003.

Dalby, "Determination of Drug Solubility in Aerosol Propellants," Pharmaceutical Research, vol. 8, No. 9, 1991, pp. 1206-1209.

Emulsifiers with HLB values. http://www.theherbarie.com/files/resources-center/formulating/Emulsifiers- .sub.--HLB.sub.--Values.pdf accessed Aug. 5, 2009 (3 pps).

Glaser, et al., Hyperhidrosis: A Comprehensive and Practical Approach to Patient Management, Expert Rev. Dermatol. 1(6), 773-775 (2006).

Hashim, et al. "Tinea versicolor and visceral leishmaniasis," Int J Dermatol., Apr. 1994; 33(4), pp. 258-259 (abstract only).

Hepburn, NC., "Cutaneous leishmaniasis," Clin Exp Dermatol, Jul. 2000; 25(5), pp. 363-370 (abstract only).

Hill, Randall M. (Ed.) Silicone Surfactants, Table of Contents and Chapter 7, "Silicone Surfactants: Applicants in the Personal Care Industry," by David T. Floyd, 1999 (30 Pages).

Hydroxyethylcellulose. Http: //terpconnect.umd.edu/-choi/MSDS/Sigma-Aldrich/HYDROXYETHYL%20CELLULOSE, 5 pages, Jan. 14, 2004.

Kalkan, et al., The Measurement of Sweat Intensity Using a New Technique, Tr. J. of Medical Sciences 28, 515-517 (1998).

Kathon.TM. CG (product information sheet by Rohm and Haas, Jun. 2006).

Kinnunen, "Skin reactions to hexylene glycol," Contact Dermatitis Sep. 1989; 21(3): 154-8.

Material Safety Data Sheet, Progesterone, Apr. 26, 2006, 5 pages.

Metronidazole. www.usp.org/pdf/EN/veterinary/metronidazole.pdf. accessed Sep. 10, 2009, 4 pages.

OM Cinnamate. http://www.makingcosmetics.com/sunscreens/OM-Cinnamate-p102.html accessed Sep. 26, 2009, 1 page.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-4 (abstract).

Shear, et al., "Pharmacoeconomic analysis of topical treatments for tinea infections," Pharmacoeconomics. Mar. 1995; 7(3); pp. 251-267 (abstract only).

Sigma Aldrich, "HLB-Numbers in Lithography Nanopatterning," http://www.sigmaaldrich.com/materials-science/micro-and-nanoelectronics/1- ithography-nanopatterning/hlb-numbers.html, accessed: Feb. 2, 2009, pp. 1-3.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).

Torres-Rodriguez, JM., "New topical antifungal drugs," Arch Med Res. 1993 Winter; 24(4), pp. 371-375 (abstract).

"Burn patients need vitamin D supplements." *Decision News Media*, Jan. 23, 2004, http://www.nutraingredients.com/Research/Burn-patients-need-vitamin-D-supplements, Accessed: May 5, 2010.

"HLB Systems", http://pharmcal.tripod.com/ch17.htm, Accessed Sep. 17, 2010, pp. 1-3.

"Minocycline" accessed on Oct. 21, 2011 at en.wikipedia.org/wiki/Minocycline, 7 pages.

"Reaction Rate" Accessed at en.wikipedia.org/wiki/Reaction_rate on Dec. 18, 2011, 6 pages.

'Niram Chemicals' [online] Niram Chemicals, [retrieved on Jul. 17, 2012]. Retrieved from the Internet: <URL: http://www.indiamart.com/niramchemicals/chemicals.html>, 7 pages.

'Surfactant' [online]. Wikipedia, 2010, [retrieved on Oct. 24, 2010]. Retrieved from the Internet: <URL: http://en.wikipedia.org/wiki/Surfactant>, 7 pages.

Adachi, Shuji. "Storage and Oxidative Stability of O/W/ Nano-emulsions." Foods Food Ingredients. J. Jpn. vol. 209, No. 11. 2004. 1 page.

Alcohol SDA 40B.http://www.pharmco-prod.com/pp./MSDS/SDA.sub.--40B.sub.--200.pdf Accessed Dec. 9, 2008, 2 pages.

Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.

Anton, N. et al. "Water-in-Oil Nano-Emulsion Formation by the phase Method: A Novel and General Concept, a New Template for Nanoencapsulation," *Proceedings of the 33rd Annual Meeting and Exposition of the Controlled Release Society*, Jul. 2006, Vienna, Austria, 2 pages.

Arct et al., "Common Cosmetic Hydrophilic Ingredients as Penetration Modifiers of Flavonoids", International Journal of Cosmetic Science, 24(6):357-366 (2002)—Abstract, 1 page.

Arisan, http://www.arisankimya.com/kozmetik.htm Accessed Dec. 10, 2008, 8 pages.

Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Barry and Badal, "Stability of minocycline, doxycycline, and tetracycline stored in agar plates and microdilution trays," *Current Microbiology*, 1978, 1:33-36.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (Nov.), p. S475 (1997), 2 pages.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no. month given). 1 page.

Croda. Aracel 165 Product Summary. 2011 (no month given). 1 page.

D.W.A. Sharp Dictionary of Chemistry, Penguin Books, 1983, 3 page.

Dawber, et al., "Hypertrichosis in Females Applying Minoxidil Topical Solution and in Normal Controls", JEADV, 17:271-275 (2003).

Denatonium Benzoate http://www.newdruginfo.com/pharmaceopeia/usp28/v28230/usp28nf23s0.sub.--m-  22790.htm Accessed Dec. 9, 2008, 2 pages.

Dentinger, et al., "Stability of Nifedipine in an Extemporaneously Compounded Oral Solution", American Journal of Health-System Pharmacy, 60(10):1019-1022 (2003)—Abstract, 1 page.

Disorder. (2007). In the American Heritage Dictionary of the English Language. Retrieved from http://www.credoreference.com/entry/hmdictenglang/disorder. 1 page.

Draelos, Z.D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). 2006 Aug; 111(2): 145-51.

Edwards, "Imiquimod in Clinical Practice", J. Am Acad Dermatol., 43(1, Pt 2):512-517 (2000)—Abstract, 1 page.

Encyclopedia of Pharmaceutical Technology, Second Edition, vol. 3, Copyright 2002, 4 pages.

Esposito, E. et al. "Nanosystems for Skin Hydration: A Comparative Study." International Journal of Cosmetic Science. 29. 2007. pp. 39-47.

Ethanol, Accessed http://www.sigmaaldrich.com/catalog/ProductDetail.do?N4=E7023SIAL&N5=SEAR-CH.sub.--CONCAT.sub.--PNOBRAND.sub.--KEY&F=SPEC Dec. 9, 2008, 2 pages.

Ethylene Oxide Derivatives: an Essence of Every Industry. A definition of Emulsifier. Http://www.emulsifiers.In/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Flick, Cosmetic and Toiletry Formulations, vol. 5, 2nd Edition, Copyright 1996, 63 pages. Relevant pp. 251-309.

Fontana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Galligan, John et al., "Adhesive Polyurethane Liners for Anterior Restorations," J. Dent. Res., Jul.-Aug. 1968, pp. 629-632.

Gelbard et al. "Primary Pediatric Hyperhidrosis: A Review of Current Treatment Options." Pediatric Dermatology. 2008. 25 (6). pp. 591-598.

Gill, A.M, et al., "Adverse Drug Reactions in a Paediatric Intensive Care Unit," Acta Paediatr 84:438-441, 1995.

Gladkikh, "Ascorbic Acid and Methods of Increasing its Stability in Drugs", Translated from Khimiko-Farmatsevticheskii Zhurnal, 4(12):37-42 (1970)—1 page.

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Gschnait, F., et al., "Topical Indomethacin Protects from UVB and UVA Irriadiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, no. 2, pp. 155-161.

Hall, Karla, "Diaper Area Hemangiomas: A Unique Set of Concerns," http://members.tripod.com/.about.Michelle.sub.--G/diaper. html, Dec. 1, 2008, 8 pages.

Hallstar. Retrieved online on Jun. 4, 2011. <URL:http://www.hallstar.com/pis.php?product=1H022>. 1 page.

Hargreaves, "Chemical Formulation, an Overview of Surfactant-Based Preparations Used in Everyday Life", *The Royal Society of Chemistry*, pp. 114-115 (2003).

Harrison, et al., "Effects of cytokines and R-837, a cytokine inducer, on Uv-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Heart Failure, the Merck Manual, 2008 <<http://www.merck.com/mmhe/sec03/ch025/ch025a.html>> 12 pages.

Hormones. Http://www.greenwillowtree.com/Page.bok?file=libido.html. Jan 2001.

http://ibabydoc.com/online/diseaseeczema.asp., Atopic Dermatitis, Copyright 2000, 6 pages.

http://web.archive.org/web/20000106225413/http://pharmacy.wilkes.edu/kibbeweb/lab7.html, Characteristics of Surfactants and Emulsions, Jan. 29, 2010, 5 pages.

http://www.agworkshop.com/p3.asp, AG&Co. Essential oil workshop. 1 page. Accessed Jan. 31, 2010.

Hubbe, Martin. Mini-Encyclopedia of Papermaking Wet-End Chemistry: Additives and Ingredients, their Composition, Functions, Strategies for Use. Retrieved online on Jun. 4, 2011. <URL:://http://www4.ncsu.edu/~hubbe/CSIL.htm>. Feb. 1, 2001. 2 pages.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03.net/com/oxymatrine/down/1249534834.pdf>. Aug. 15, 2009. 3 pages.

Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

Izquierdo, P. et al. "Formation and Stability of Nano-Emulsions Prepared Using the Phase Inversion Temperature Method." University of Barcelona. Sep. 17, 2001. 1 page.

Jan. "Troubled Times: Detergent Foam." http://zetatalk.com/health/theal17c.htm. Accessed Feb. 9, 2012. 2 pages.

Joseph, "Understanding foams & foaming," University of Minnesota (1997), at http://www.aem.umn.edu/people/faculty/joseph/archive/docs/understandingfoams.pdf, pp. 1-8.

Kanamoto, et al., "Pharmacokinetics of two rectal dosage forms of ketoprofen in patients after anal surgery," J Pharmacobiodyn., Mar. 1988; 11(3):141-5.

Kang, et al., "Enhancement of the Stability and Skin Penetration of Vitamin C by Polyphenol", Immune Netw., 4(4):250-254 (2004)—Abstract, 1 page.

Karasu, T.B. et al., "Treatment of Patients with Major Depressive Disorder, Second Edition," pp. 1-78, 2000.

Kim, "Stability of Minoxidil in Aqueous Solution", Yakhak Hoechi, 30(5):228-231 (1986)—Abstract, 1 page.

Kleber, M.D., H.D. et al., "Treatment of Patients with Substance Use Disorders, Second Edition," pp. 1-276, 2006.

Koerber, S., "Humectants and Water Activity," Water Activity News, 2000, ISSN No. 1083-3943.

Kreuter, J. "Nanoparticles and microparticles for drug and vaccine delivery," J. Anat. (1996) 189, pp. 503-505.

Kumar, J. et ak., "Application of Broad Spectrum Antiseptic Povidone Iodine as Powerful Action: A Review," Journal of Pharmaceutical Science and Technology vol. 1(2), 2009, 48-58.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." *J Am. Acad. Dermatol.* 45:487-498. Oct. 2001.

Lebwohl et al., "A randomized, double-blind, placebo-controlled study of clobestasol propionate 0.05% foam in the treatment of nonscalp psoriasis," *International Journal of Dermatology*, 2002, 41(5): 269-274.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Leung, et al., "Bioadhesive Drug Delivery in Water-Soluble Polymers," American Chemical Society, Chapter 23, 1991, pp. 350-366.

Li, et al., "Solubility Behavior of Imiquimod in Alkanoic Acids", Abstract 3029, Pharmaceutical Research, vol. 14, No. 11 Supplemental (Nov.), p. S475 (1997), 2 pages.

Licking Vaginal Dryness without a Prescription. Accessed http://www.estronaut.com/a/vag.sub.-- dryness.htm on Dec. 14, 2008, 3 pages.

Lippacher, A. et al. "Liquid and Semisolid SLN Dispersions for Topical Application" Rheological Characterization. European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Martindale, the extra pharmacopoeia [28th] edition, Eds.: Reynolds, J.E.F. And Prasad, A.B., The Pharmaceutical Press, London, pp. 862-864, 1982.

Martindale. 33 ed. London, Bath Press, 2002. pp. 1073 and 1473.

Material Safety Data Sheet, Science Lab.com, Polyethylene Glycol 1000, MSDS, Nov. 6, 2008, 6 pages.

Merck index, 10th edition, Merck & Co., Inc.: Rahway, NJ, 1983, pp. 39 (entry 242 for allantoin).

Merck index, 14th edition, O'Neill, ed., 2006, entry for p-amino benzoic acid.

Merck index, 14th edition, O'Neill, ed., 2006, entry for zinc oxide.

Merck Index, An Encyclopedia of Chemicals, Drugs, and Biologicals. 13$^{th}$ Edition. O'Neil et al eds. Entries 1058, 2350, 6143, and 8803. 2001. 7 pages.

Merck Manual Home Edition. "Excessive Sweating: Sweating Disorders." Accessed Apr. 14, 2011 at www.merckmanuals.com/home/print/sec18/ch206/ch206c.html. 2 pages.

Merriam Webster Online Dictionary [online] retrieved from http://www.merriam-webster.com/cgi-bin/dictionary?book=dictionary&va=derivative on Jul. 5, 2008; 1 page.

Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3- 4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://ww.cosmetoscope.com/2010/04/neutrogea-clinical-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.
No Author Listed. "Opitmization of Nano-Emulsions Production by Microfluidization." European Food Research and Technology. vol. 225, Nos. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
Padhi et al., "Phospho-olicines as positive-electrode materials for rechargeable lithium batteries," *J. Electrochemical Soc.*, 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.
Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
prevent. (2007). In The American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural 503-507 and synthetic triphylite," *J. Of Power Sources*, 2001, 97-98: 503-507.
Raymond, Iodine as an Aerial Disinfectant, Journal of Hygiene, vol. 44, No. 5 (May, 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, *Langmuir*, 2006, 22: 8337-8345.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum--Copper-Peptide Serum for Skin Regeneration and Reducing Wrinkles, Skin Biology, http://web.archive.org/web/20030810230608/http://www.skinbio.com/cpserum.-   html, Dec. 1, 2008, 21 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pp. 145-149.
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, *J. Invest. Dermatol.*, 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (Nov.), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: The Complete Drug Reference. 33rd Edition. London. Pharmaceutical Press. Jun. 21, 2002. pags. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate -1. Accute toxicity of hydrocortisone 17-butyrate 21-propionate and its analogues in mice, rats and dogs (author's trans), J Toxicol Sci., Jul. 1981; 6 Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb 4, 2009, 4 pages, cited by other.
Toxicology and Carcinogenesis Studies of t-Butyl Alcohol (Cas No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.

Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Yamada and Chung, "Crystal Chemistry Possible 4 V Cathode Materials for Lithium 967 of the Olivine-Type Li($Mn_yFei_{1-y}$)$PO_4$ and ($Mn_yFei_{1-y}$)$PO_4$ as Possible 4 V Cathode Materials for Lithium Batteries," J. Electrochemical Soc., 2001, 148(8): A960-967.
"Coal tars and coal-tar pitches," Report on Carcinogens, Twelfth Edition, 2011, 3 pages.
Adisen et al. "Topical tetracycline in the 7:953-5 treatment of acne vulgaris," J Drugs Dermatol., 2008, 7:953-5.
Baskaran et al., "Poloxamer-188 improves capillary blood flow and tissue viability in a cutaneous burn wound," J. Surg. Res., 2001, 101(1):56-61.
Bell-Syer et al. "A systematic review of oral treatments for fungal infections of the skin of the feet," J. Dermatolog. Treat., 2001, 12:69-74.
Boehm et al. 1994, "Synthesis of high specific activity [.sup.3 H]-9-cis-retinoic acid and its application for identifying retinoids with unusual binding properties," J. Med. Chem., 37:408-414;.
Carapeti et al., "Topical diltiazem and bethanechol decrease anal sphincter pressure and heal anal fissures without side effects," Dis Colon Rectum, 2000, 43(10):1359-62.
Cook and Mortensen, "Nifedipine for treatment of anal fissures," Dis Colon Rectum, 2000, 43(3):430-1.
Dumortier et al., "A review of poloxamer 407 pharmaceutical and pharmacological characteristics," Pharmaceutical Res., 2006, 23(12):2709-2728.
Ebadi et al., "Healing effect of topical nifedipine on skin wounds of diabetic rats," DARU, 2003, 11(1):19-22.
Effendy and Maibach. "Surfactants and Experimental Irritant Contact Dermatol." Contact Dermatol., 1995, 33:217-225.
Elias and Ghadially, "The aged epidermal barrier," Clinical Geriatric Medicine, Feb. 2002, pp. 103-120.
Fantin et al., "Critical influence of resistance to streptogramin B-type antibiotics on activity of RP 59500 (Quinupristin-dalfopristin) in experimental endocarditis due to Staphylococcus aureus," Antimicrob Agents and Chemothery, 1999, 39:400-405.
Fluhr et al., "Glycerol accelerates recovery of barrier function in vivo," Acta Derm. Venereol,. 1999, 79:418-21.
Garti et al. "Sucrose Esters microemulsions," J. Molec. Liquids, 1999, 80:253-296.
Hammer et al. "Anti-Microbial Activity of Essential Oils and other Plant Microbiology," J. Applied Microbiology, 1999, 86:985-990.
Hwang et al. "Isolation and identification of mosquito repellents in Artemisia vulgaris," J. Chem. Ecol., 11: 1297-1306, 1985.

Knight et al., "Topical diltiazem ointment in the treatment of chronic anal fissure," Br. J. Surg., 2001, 88(4):553-6.
Kucharekova et al., "Effect of a lipid-rich emollient containing ceramide 3 in experimentally induced skin barrier dysfunction," Contact Dermatitis, Jun. 2002, pp. 331-338.
Leive et al, "Tetracyclines of various hydrophobicities as a probe for permeability of Escherichia coli outer membrane," Antimicrobial Agents and Chemotherapy, 1984, 25:539-544.
Luepke and Kemper, "The HET-CAM Test: An Alternative to the Draize Eye Test," FD Chem. Toxic., 1986, 24:495-196.
Osborne and Henke, "Skin Penetration Enhancers Cited in the Technical Literature," Pharm. Technology, Nov. 1997, pp. 58-86.
Padi. "Minocycline prevents the development of neuropathic pain, but not acute pain: possible anti-inflammatory and antioxidant mechanisms," Eur J. Pharmacol, 2008, 601:79-87.
Palamaras and Kyriakis, "Calcium antagonists in dermatology: a review of the evidence and research-based studies," Derm. Online Journal, 2005, 11(2):8.
Passi et al., Lipophilic antioxidants in human sebum and aging, Free Radical Research, 2002, pp. 471-477.
Perrotti et al., "Topical Nifedipine With Lidocaine Ointment vs. Active Control for Treatment of Chronic Anal Fissure," Dis Colon Rectum, 2002, 45(11):1468-1475.
Repa et al. "All-trans-retinol is a ligand for the retinoic acid receptors," Proc. Natl. Acad Sci, USA, 90: 7293-7297, 1993.
Ruledge, "Some corrections to the record on insect repellents and attractants," J. Am. Mosquito Control Assoc, 1988, 4(4):414-425.
Sakai et al., "Characterization of the physical properties of the stratum corneum by a new tactile sensor," Skin Research and Technology, Aug. 2000, pp. 128-134.
Schaefer, "Silicone Surfactants," Tenside, Surfactants, Deterg., 1990, 27(3): 154-158.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Smith, "Hydroxy acids and skin again," Soap Cosmetics Chemical Specialties, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," European J. Pharm. Biopharm., 1998, 46(3):265-71.
Todd et al. "Volatile Silicone Fluids for Cosmetics," 91 Cosmetics and Toiletries, 1976, 27-32.
Torma et al., "Biologic activities of retinoic acid and 3, 4-dehydroretinoic acid in human keratinoacytes are similar and correlate with receptor affinities and transactivation properties," J. Invest. Dermatology, 1994, 102: 49-54.
USP23/NF 18 the United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," J. Biol. Chem., 1922, 52:525.
Van Cutsem et al., "The antiinflammatory efects of ketoconazole," J. AM. ACAD. Dermatol., 1991, (2 pt 1):257-61.
Wang and Chen, "Preparation and surface active properties of biodegrabable dextrin derivative surfactants," Colloids and Surfaces A: Physicochemical and Engineering Aspects, 2006, 281(1-3):190-193.
Weindl et al., "Hyaluronic acid in the treatment and prevention of skin diseases: molecular biological, pharmaceutical and clinical aspects," Skin Pharmacology and Physiology, 2004, pp. 207-213.
Xynos et al., "Effect of nffedipine on rectoanal motility," Dis Colon Rectum, 1996, 39(2):212-6.
Yamada et al., "Candesartan, an angiotensin II receptor antagonist, suppresses pancreatic inflammation and fibrosis in rats," J. Pharmacol. Exp. Ther., 2003, 307(1)17-23.
Paragraph E.3.1 of regulation (EC) No. 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. "Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

Skin Deep Cosmetics. PPG-40-PEG-60 Lanolin Oil http://www.cosmeticsdatabase.com/ingredient/722972/PPG-40-PEG60_Lanolin_Oil/?ingred06=722972. 2010, 3pages.

\* cited by examiner

PENETRATING PHARMACEUTICAL FOAM

RELATED APPLICATIONS

This application is a divisional application under 35 U.S.C. §121 of co-pending U.S. patent application Ser. No. 10/922,358 filed on Aug. 20, 2004, entitled "Penetrating Pharmaceutical Foam." U.S. patent application Ser. No. 10/922,358 claims the benefit under 35 U.S.C. §119(e) to U.S. Patent Application No. 60/497,648 filed on Aug. 25, 2003. U.S. patent application Ser. No. 10/922,358 is also (1) a continuation-in-part of International Application No. IB03/005527 filed on Oct. 24, 2003, which claims the benefit under 35 U.S.C. 119(e) to U.S. Patent Application No. 60/429,546 filed on Nov. 29, 2002, and (2) a continuation-in-part of U.S. patent application Ser. No. 10/911,367 filed on Aug. 4, 2004, which claims the benefit under 35 U.S.C. §119(e) to U.S. Patent Application No. 60/492,385 filed on Aug. 4, 2003. The contents of all of the patent applications referenced in this paragraph are hereby incorporated in their entirety by reference.

FIELD OF THE INVENTION

The invention relates to an alcohol-free cosmetic or pharmaceutical foam carrier comprising water, a hydrophobic solvent, a surface-active agent and a gelling agent. The foam carrier further comprises active agents and excipients providing beneficial therapeutic properties.

BACKGROUND OF THE INVENTION

Foam products are used for topical applications of drugs and cosmetics. Aerosol products and particularly foams are complicated physical-chemical structures that do not form under arbitrary circumstances. In particular, a special balance between the foam-forming components is important. Slight shifts in the composition may already result in a collapse of the foam; thus, a formulation of per se active substances may not be capable of being formulated as a foam without further provisions.

The inventors of the present invention have developed a series of novel emulsion-based foam formulations. See, for example, commonly assigned, co-pending application WO 2004/037225.

U.S. Pat. No. 6,423,323 describes a foam skin cream, which optionally contains urea and lactic acid. The skin cream formulation is limited to a very specific list of ingredients that are not contemplated in the present invention.

U.S. Pat. No. 4,145,411 describes shaving foam compositions with low levels of mineral oil (0.25-1% by weight) and urea (0.001-0.006% by weight). A shaving foam is, by definition, not breakable and thus cannot readily facilitate topical administration of an active ingredient and especially is not well-suited for topical administration of compositions geared towards skin penetration.

SUMMARY OF THE INVENTION

In one aspect of the present invention, an alcohol-free cosmetic or pharmaceutical foamable composition containing at least one active component, selected from the group of: (1) urea, in a concentration of at least 2%; (2) a hydroxy acid in a concentration of at least 1%; and (3) a therapeutic enhancer is provided, which upon admixing with a liquefied gas propellant in an aerosol container releases a breakable foam that is suitable for topical administration. The alcohol-free foam composition is suitable for inclusion of both water-soluble and oil-soluble active agents. As used herein, a foamable composition includes formulations that are capable of forming a foam when dispensed from an aerosol container.

The cosmetic or pharmaceutical foamable composition according to one or more embodiments of the present invention includes water, a hydrophobic solvent, a surface-active agent and a gelling agent and at least one active component selected from the group of (1) urea in a concentration of at least 2%; (2) a hydroxy acid in a concentration of at least 1%; and (3) a therapeutic enhancer in a concentration of at least 2%; and a liquefied gas propellant in the amount of about 3-18% by weight of the total composition.

Such a composition creates an oil-in-water emulsion that is stable in its pre-dispensed state. Upon release from the aerosol container, the composition forms a breakable foam product, which is suitable for topical or mucosal administration.

In one or more embodiments of the present invention, the hydrophobic solvent is included in the foamable composition at a concentration of 5% to about 10% (Class A), or 10% to about 20% (Class B), or about 20% to about 50% (Class C). The surface-active agent concentration is about 0.1% to about 5%; the concentration of the gelling agent is 0.01% to about 5% by weight and the liquefied gas propellant is included at a concentration of about 3% to about 18% of the total composition. Water and optional ingredients are added to complete the total mass to 100%. Yet, in other embodiments, as specified herein, foamable composition, the hydrophobic solvent content can be between 0% and 5%.

In one or more embodiments, each of the above compositions further optionally comprises a foam adjuvant in the concentration range of 0.1% to 5%.

The foamable composition does not contain short chain aliphatic alcohols, making it non-irritant and non-drying.

In one or more embodiments, a foamable composition is provided that includes a foamable composition as described herein and further includes at least one active agent at a therapeutically effective concentration. The foam carrier is suitable for inclusion of both water-soluble and oil-soluble active agents, as well as suspended active agents. Such a composition is suitable for topical treatment of human and animal skin and mucosal disorders or diseases. Alternatively, the composition is suitable for cosmetic treatment, for example, for cleansing, beautifying, promoting attractiveness or altering the appearance without affecting the body structure or function.

In addition, cosmetic and medical disorders are identified that are best treated using the alcohol-free foam carrier and the alcohol-free cosmetic or pharmaceutical composition, and the advantages of such carrier and products are demonstrated.

The foam carrier or composition according to one or more embodiments of the present invention provides various advantages over current foam compositions.
1. The foam is lightweight and thus, economical.
2. The foam contains a hydrophobic solvent, in desirable concentration, which provides a refatting and skin soothing effect.
3. The foam can include water-soluble, oil-soluble active and suspended agents.
4. The foam is easily spreadable, allowing treatment of large areas such as the arms, back, legs and the breast.
5. Due to flow properties of the foam, the foam spreads effectively into folds and wrinkles, thereby providing uniform distribution and absorption of the active agent without the need of extensive rubbing.

As used herein, all component percentages are reported as percent by weight of the total composition.

As used herein, the term "about" when used to refer to weight % in a composition means±10% of the reported weight %. As used herein, the term "about" when used to refer to measured characteristics of the composition means±20% of the reported value.

DETAILED DESCRIPTION OF THE INVENTION

Hydrophobic Solvent

The foamable composition includes a hydrophobic solvent. The hydrophobic solvent includes a material having solubility in distilled water at ambient temperature of less than about 1 gm per 100 mL, or less than about 0.5 gm per 100 mL, or less than about 0.1 gm per 100 mL. The hydrophobic solvent is a liquid at ambient (room) temperature, e.g., about 20-30° C.

The total content of hydrophobic solvent may vary from 5% to 50% (w/w). However, different ranges (herein "composition Classes A-C") have been designated, in order to facilitate a choice of an appropriate class, according to the anticipated cosmetic or pharmaceutical need. As a rule of thumb, higher hydrophobic solvent concentrations are more appropriate for the treatment of dry skin, and/or for the treatment of a disease, which is more responsive to drugs, delivered in an oily vehicle and regulating the residence of an active ingredient in the target area. Another consideration relates to the usability and tolerability of the product, whereby very high concentration of the hydrophobic solvent (from about 25% of the composition) would leave an oily feeling subsequent to application, which is undesirable in the product. Thus, when using a foamable composition, the hydrophobic solvent concentration is selected in view of the target treated population and the specific needs of the intended treated population.

In one embodiment, the hydrophobic solvent is mineral oil. Mineral oil (Chemical Abstracts Service Registry number 8012-95-1) is a mixture of aliphatic, naphthalenic, and aromatic liquid hydrocarbons that derive from petroleum. They are typically liquid, their viscosity is in the range of between about 35 CST and about 100 CST (at 40° C.), and their pour point (the lowest temperature at which an oil can be handled without excessive amounts of wax crystals forming so preventing flow) is below 0° C. By contrast, white petrolatum, also termed "Vaseline", is disadvantageous, due to the waxy nature of petrolatum. It is known to leave waxy and sticky feeling after application and occasionally stain cloths. Thus, white petrolatum is not a preferred hydrophobic solvent according to the present invention.

Yet other hydrophobic solvents include, but are not limited to, liquid oils from vegetable, marine or animal sources. Preferably, the unsaturated oil is selected from the group consisting of an olive oil, a corn oil, a soybean oil, a canola oil, a cottonseed oil, a coconut oil, a sesame oil, a sunflower oil, a borage seed oil, an syzigium aromaticum oil, a hempseed oil, a herring oil, a cod-liver oil, a salmon oil, a flaxseed oil, a wheat germ oil, an evening primrose oil and any mixtures thereof, at any proportion.

A particular class of oils includes polyunsaturated oils, containing omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Thus, in a particular embodiment of the present invention the unsaturated oil contains at least 6% of an oil selected from omega-3 oil, omega-6 oil, and mixtures thereof.

Another class of oils is essential oils, which are considered "therapeutic oils" containing active biologically occurring molecules, which, upon topical application, exert a therapeutic effect. Examples of such oils are rosehip oil, which contain retinoids and is known to reduce acne and post-acne scars, tea tree oil, which possesses antibacterial, antifungal and antiviral properties. Other examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla, verbena, as well as any other therapeutically beneficial oil, know in the art of herbal medication.

Another class of solvents includes, but is not limited to, liquid hydrophobic plant-derived oils, which are known to possess therapeutic benefits when applied topically.

A further class of hydrophobic solvents is known as the group of "emollients". Without derogating the generality of this definition, examples of suitable emollients for use include isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristal myristate, triisocetyl citrate, octyl dodecanol, sucrose esters of fatty acids, octyl hydroxystearate and mixtures thereof. Other examples of other suitable emollients can also be found in the Cosmetic Bench Reference, pp. 1.19-1.22 (1996).

In a particular embodiment, the hydrophobic solvent comprises a mixture of mineral oil and an emollient in a ratio between 2:8 and 8:2 on a weight basis.

Silicone oils are known for their skin protective properties and may be used as a hydrophobic solvent. The silicone oil is either a volatile silicon oil or a non-volatile silicone oil, wherein water-soluble silicones, such as dimethicone copolyol are not included in the definition of silicone oils (as hydrophobic solvents).

In a particular embodiment, the hydrophobic solvent includes at least 2% silicone oil.

One or more hydrophobic solvents in any combination can be used.

Surface-active Agents

The foamable composition includes a surface-active agent. Surface-active agents (surfactants) include any agent that alters the surface properties of the oil and water components in the composition to aid in the formation of an emulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers tend to form water-in-oil (w/o) emulsions; hydrophilic surfactants tend to form oil-in-water (o/w) emulsions. The HLB of a blend of two emulsifiers equals the weight fraction of emulsifier A times its HLB value plus the weight fraction of emulsifier B times its HLB value (weighted average).

Any surface-active agent, selected from anionic, cationic, non-ionic, zwitterionic, amphoteric and ampholytic surfactants, or combinations thereof may be used as surface-active agent. According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition is a single surface active agent having an HLB value between about 9 and 14, and in one or more embodiments, the foam composition contains more than one surface active agent and the weighted average of their HLB values is between about 9 and about 14.

Non-limiting examples of surfactants include polysorbates, such as polyoxyethylene (20) sorbitan monostearate (Tween 60) and polyoxyethylene (20) sorbitan monooleate (Tween 80); Polyoxyethylene (POE) fatty acid esters, such as Myrj 45, Myrj 49 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and sorbitol anhydrides, such as sorbitan monolaurate and sorbitan monolaurate-mono or diglycerides, isoceteth-20, sodium methyl cocoyl taurate, sodium methyl oleoyl taurate, sodium lauryl sulfate, triethanolamine lauryl sulfate and betaines.

In some embodiments, the surface-active agent is a non-ionic surfactant. Exemplary non-ionic surfactants include mono-, di- and tri-esters of sucrose with food fatty acids (sucrose esters), prepared from sucrose and methyl and ethyl esters of food fatty acids or by extraction from sucroglycerides. Further examples are sucrose esters with high monoester content, which have higher HLB values.

A combination of a non-ionic surfactant and an ionic surfactant (such as sodium lauryl sulphate) may be used. In one example, a non-ionic surfactant and an ionic surfactant are present in the foam carrier or composition at a ratio of between 1:1 and 20:1 or between 4:1 and 10:1.

Unlike prior art foamable compositions, low total amounts of surfactant are employed to obtain a stable foam. Surprisingly, lower surfactant levels are required to obtain a stable foamable composition, which is preferred in order to reduce skin irritations. Total surfactant level is in the range of about 0.1% to 5% by weight of the foamable composition, and can be less than 2% by weight or even less than 1% by weight. Thus, according to one or more embodiments, the ratio between the surface active agent and the hydrophobic solvent is between about 1:8 and about 1:16 or between about 1:16 and about 1:32.

Foam Adjuvants

Foam adjuvants may optionally be included in the foam composition and include fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). The concentration of the fatty alcohol, required to support the foam system is inversely related to the length of its carbon chains. Fatty alcohols derived from beeswax including a mixture of alcohols, a majority of which has at least 20 carbon atoms in their carbon chain, are especially well suited as foam adjuvants.

Another class of foam adjuvants includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof.

Optionally, the carbon atom chain of the fatty alcohol or the fatty acid may have at least one double bond. A further class of foam adjuvant includes a long chain fatty alcohol or fatty acid, wherein the carbon atom chain is branched. In a further class of foam adjuvants, the carbon chain of the fatty acid is substituted with a hydroxyl group, such as 12-hydroxy stearic acid.

The foam adjuvant may include a mixture of fatty alcohols, fatty acids and hydroxy fatty acids and derivatives thereof in any proportion, providing that the total amount is 0.1% to 5% (w/w) of the carrier mass. The total amount can be 0.4%-2.5% (w/w) of the carrier mass.

Long chain saturated and mono unsaturated fatty alcohols, e.g., stearyl alcohol, erycyl alcohol, arachidyl alcohol and docosanol have been reported to possess antiviral, anti infective, anti-proliferative and anti-inflammatory properties (U.S. Pat. No. 4,874,794). Longer chain fatty alcohols, e.g., tetracosanol, hexacosanol, heptacosanol, octacosanol, triacontanol, etc. are also known for their metabolism modifying properties and tissue energizing properties. Long chain fatty acids have also been reported to possess anti-infective characteristics. Thus, the pharmaceutical or cosmetic composition containing therapeutic foam adjuvant provides an extra therapeutic benefit in comparison with currently used vehicles, which are inert and non-active.

Gelling Agents

Gelling agents include, but are not limited to, naturally-occurring polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), micro-crystalline cellulose and compositions (Avicel types) manufactured by FMC, polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Optionally, mixtures of the above compounds are contemplated.

Also useful herein are gelling agents such as the acrylic acid/ethyl acrylate copolymers and the carboxyvinyl polymers sold, for example, by the B.F. Goodrich Company under the trademark of Carbopol Registered TM resins. These resins consist essentially of a colloidally water-soluble polyalkenyl polyether crosslinked polymer of acrylic acid crosslinked with from 0.75% to 2% of a crosslinking agent such as polyallyl sucrose or polyallyl pentaerythritol. Examples include Pemulene TR1 and TR2, Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 alkyl groups for each sucrose molecule.

In one aspect of the invention, the gelling agent is selected from the class of amphiphilic copolymers. Amphiphilic copolymers include polymers having hydrophobic groups and hydrophilic groups or regions. These materials are referred to alternatively as "polymeric surfactants" because the hydrophilic and hydrophobic regions of the polymers serve to interact with and stabilize hydrophilic and lipophilic components, respectively, of a composition. The copolymer may be a random copolymer, a block copolymer of a graft or comb copolymer. Exemplary amphiphilic copolymers include di-, tri- or multi-block copolymer or graft copolymer of a biodegradable polymer.

The Amphiphilic copolymer may be an acrylate copolymer, in which hydrophobic moieties are chemically linked to hydrophilic polymer or hydrophilic moieties are attached to hydrophobic polymers to produce amphiphilic surface active and surface stabilizing agent. By way of example, suitable amphiphilic copolymers include cross linked copolymers of acrylic acid and a hydrophobic comonomer, such as Pemulen TR-1 and Pemulen TR-2, ETD 2020 and Carbopol 1382 (all, Acrylates/C10-30 alkyl acrylate crosspolymer), Natrosol CS Plus 330 and 430 and Polysurf 67 (all, cetyl hydroxyethyl cellulose), Aculyn 22 (acrylates/steareth-20 methacrylate copolymer), Aculyn 25 (acrylates/laureth-25 methacrylate copolymer), Aculyn 28 (acrylates/beheneth-25 methacrylate copolymer), Aculyn 46 (PEG-150/stearyl alcohol/SMDI copolymer), Stabylen 30 (acrylates/vinyl isodecanoate), Structure 2001 (acrylates/steareth-20 itaconate copolymer), Structure 3001 (acrylates/ceteth-20 itaconate copolymer) and Structure Plus (acrylates/aminoacrylates/C10-30 alkyl PEG 20 itaconate copolymer), where PEG is polyethylene glycol, PPG is polypropylene glycol.

Other exemplary amphiphilic copolymers include silicone polymers such as amphiphilic silicone polyols or copolyol, for example cetyl dimethicone copolyol and dimethicone copolyol PPG-3 oleyl ether, acetylated starch derivatives, amphiphilic modified starches, and amphiphilic block copolymers of ethylene oxide, propylene oxide and/or propylene glycol (also known as "poloxamer").

One or more gelling agents in any combination can be used.

The gelling agent is present in the foam composition in an amount of about 0.1% to 5.0%. In one or more embodiments, the gelling agent included in the foamable composition can be less than 1% of the foamable composition.

Active Component

According to one or more embodiments, urea is included in the foam composition as an active component.

Urea has been long recognized as a cosmetic ingredient in formulations acting as a humectant and moisturizer. There have been reports of keratolytic activity attributed to urea with the ability at high concentrations to solubilize and denature protein. High concentrations of urea are also known to have a mild, antimicrobial effect. Urea further possesses skin exfoliating properties, which are useful in the control of passage of active agents through the dermal barrier.

Urea preparations, especially those containing high urea concentration are provided in gels, creams, lotions and pastes, but not in foam. Foam is preferable in many cases where urea is needed for therapy. For example, xerosis, which is a common indication for high concentration urea preparations, is disseminated over large skin areas, and thus, the foam of the present invention, having low specific gravity and excellent spreading and absorption properties is advantageous.

In one embodiment, urea is contained in the foam composition in an amount from about 1% to about 50% of the total composition. Preferably compositions contain from about 10% to about 20%, and from about 20% to about 50%, depending on the intended use.

Because of its keratolytic effect, urea can serve as means to induce dermal penetration of a variety of drugs or cosmetic active agents. Furthermore, in many dermatological disorders, having urea, with its beneficial properties as mentioned above and a drug or cosmetic active agent provides a synergistic therapeutic effect. This is also the case when urea, which is known for its antibacterial and antifungal effects, is combined with another anti-infective agent.

Thus, in one or more embodiments of the present invention, the foamable composition includes urea and at least one pharmaceutical or cosmetic active agent, as defined hereinbelow. The penetration of the active agent is enhanced due to the urea present in the foam composition.

Hence, a foam according to the present invention includes a foamable composition containing urea in a therapeutically—effective concentration. In one embodiment, the foamable composition forms an emulsion of oil and water including a hydrophobic solvent at a level described herein as Class A, Class B, or Class C.

According to one or more embodiments, a hydroxy acid is included in the foam composition as an active component.

Hydroxy acids are useful in increasing the clarity of the skin surface, increasing cellular turnover, and increasing skin radiance and smoothness. They further possess skin exfoliating properties, which are useful in the control of passage of active agents through the dermal barrier.

Suitable hydroxy acids include alpha- or beta-hydroxy acids, poly-hydroxy acids, or any combinations of any of the foregoing. The hydroxy acid can be an alpha-hydroxy acid. Non-limiting examples of alpha hydroxy acids include, but are not limited to, glycolic acid, lactic acid, malic acid, citric acid, alpha-hydroxyethanoic acid, alpha-hydroxyoctanoic acid, alpha-hydroxycaprylic acid, hydroxycaprylic acidglycolic acid, tartaric acid, pyuric acid, citric acid, as well as their corresponding salts and pharmaceutically-acceptable derivatives; or any combination of any of the foregoing.

Ascorbic acid has skin permeation and collagen synthesis activity. Beta-hydroxy acids include, but are not limited to, salicylic acid, beta hydroxybutanoic acid, tropic acid and trethocanic acid.

Because of its keratolytic effect, hydroxy acids can serve as means to induce dermal penetration of a variety of drugs or cosmetic active agents. Furthermore, in many dermatological disorders, having urea, with its beneficial properties as mentioned above and a drug or cosmetic active agent provides a synergistic therapeutic effect.

Thus, in one or more embodiments of the present invention, the foamble composition comprises a hydroxy acid and at least one pharmaceutical or cosmetic active agent, as defined hereinbelow.

In one embodiment, the hydroxy acid is contained in the foamable composition in an amount from about 1% to about 30% of the total composition. The compositions can contain from about 1% to about 10% and from about 10% to about 30%, depending on their designated use.

According to one or more embodiments, a therapeutic enhancer is included in the foam composition as an active component. In the context of the present invention, a therapeutic enhancer is a material that facilitates an enhanced delivery of an active agent into a target site of treatment, thus enabling an improved therapeutic effect. Suitable therapeutic enhancers include polyhydric alcohols having at least two hydroxy groups, or at least three hydroxy groups, or a derivative of a polyhydric alcohol.

Non-limiting examples are propylene glycol, butylene glycols, glycerol, pentaerythritol, sorbitol, mannitol, oligosaccharides, dimethyl isosorbide, monooleate of ethoxylated glycerides (with 8 to 10 ethylene oxide units), polyethylene glycol 200-600, transcutol (diethylene glycol monoethyl ether) and glycofurol (tetrahydrofurfuryl alcohol PEG ether). The therapeutic enhancer can further comprise at least cyclodextrins a related compounds. Cyclodextrins are structurally related cyclic oligomaltoses, which form a new group of pharmaceutical excipients. These are torus-shaped molecules with a hydrophilic outer surface and a lipophilic central cavity. Cyclodextrins are capable of forming water-soluble inclusion complexes with a wide variety of lipophilic water-insoluble drugs by taking up a whole drug molecule, or some part of it, into the cavity. The cyclodextrin molecules are relatively large (molecular weight ranging from almost 1000 to over 1500), with a hydrated outer surface, and under normal conditions, cyclodextrin molecules will only permeate the skin barrier with considerable difficulty. It is generally believed that the cyclodextrin molecules act as true carriers by keeping lipophilic drug molecules in solution and deliver them to the skin surface where they partition from the cyclodextrin cavity into the skin.

In one embodiment, the therapeutic enhancer is contained in the foamable composition in an amount from about 2% to about 30% of the total composition. The compositions can contain from about 2% to about 10% and from about 10% to about 30%, depending on their designated use.

Active Agents

The foam composition is useful and advantageous for the treatment of skin disorders and for skin care and cosmetic care. The addition of an oil having refatting, protective and moisture-retaining properties in a spreadable foam form can substitute for currently available dermatological and cosmetic creams, lotions, gels, etc.

In one or more embodiments of the present invention, the foam composition includes an active agent directed to the treatment of a medical disorder or a cosmetic disorder. The active agent can be categorized by the benefit it provides or by its postulated mode of action. The active agents can in some instances provide more than one benefit or operate via more than one mode of action. Therefore, classifications are made for the sake of convenience and are not intended to limit the active to that particular application or applications listed. Furthermore, foam compositions, with or without further active ingredients, are suitable for the application as "cosmeceutical" preparations.

Antibacterial Agents

One class of drugs comprises antibacterial agents. The term "antibacterial" as used herein shall include, but is not limited to, any substance being destructive to or inhibiting the growth of bacteria or any substance having the capacity to inhibit the growth of or to destroy bacteria and other microorganisms, and are used in the treatment of infectious diseases. It is well known that bacterial infections are involved in a variety of superficial disorders of the skin, eye, mucosal membrane, oral cavity, vagina and rectum. The antibacterial drug can be active against gram positive and gram-negative bacteria, protozoa, aerobic bacteria and unaerobic ones.

The antibacterial drug is selected from the group consisting of chloramphenicol, tetracyclines, synthetic and semi-synthetic penicillins, beta-lactams, quinolones, fluoroquinolnes, macrolide antibiotics, metronidazole and metronidazole derivatives and analogs, dicarboxylic acids, such as azelaic acid, silicylates, peptide antibiotics, cyclosporines and any combination thereof at a therapeutically effective concentration. Another group of antibacterial agents is non-specific and includes strong oxidants and free radical liberating compounds, such as hydrogen peroxide, bleaching agents (e.g., sodium, calcium or magnesium hypochlorite and the like) iodine, chlorohexidine and benzoyl peroxide.

Exemplary foamable compositions are particularly useful and beneficial in the prevention and treatment of secondary infections, accompanying skin-structure damage, such as in cuts, wounds, burns and ulcers. In all such cases, the present formulation is easy to use, being in foam state when applied and becoming liquid upon rubbing onto the skin.

While being useful in the prevention and treatment of infections, the antibacterial foam is also applicable for decontaminating areas, afflicted with bacterial warfare organisms, such as anthrax and smallpox.

Anti-fungal Agents

Fungal infections are another object of treatment using the foamable composition. Superficial fungal infection of the skin is one of the commonest skin diseases seen in general practice. Dermatophytosis is probably the most common superficial fungal infection of the skin. Dermatophytosis is caused by a group of fungi capable of metabolizing the keratin of human epidermis, nails or hair. There are three genera of dermatophytes causing dermatophytosis, i.e., microsporum, trichophyton and epidermophyton.

Candidiasis is an infection caused by the yeast like fungus candida albicans or occasionally other species of candida. Clinical syndromes of candidiasis include: (a) oral candidiasis (oral thrush); (b) candidiasis of the skin and genital mucous membrane; (c) candida paronychia, which inflicts the nail; and (d) genital and vaginal candida, which inflict genitalia and the vagina.

The pharmaceutical composition can include an antifungal drug that is effective against dermatophytes and candida. The antifungal drug is selected from the group consisting of azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration.

The foam composition according to one or more embodiments of the present invention is useful, for example, for the treatment of tinea corporis, tinea pedis, tinea rubrum, tinea unguium, tinea cruris, tinea barbae and tinea versicolor, as well as yeast Infections, such as candidiasis, and candidal vaginitis.

Anti-viral Agents

Any known antiviral drugs, in a therapeutically effective concentration, can be incorporated into the foam composition. Exemplary compositions are particularly beneficial in the case of viral infections. Cold sores are caused by the herpes simplex Type 1 virus and are sometimes referred to as facial herpes. Mollusca are small viral growths that appear singly or in groups on the face, trunk, lower abdomen, pelvis, inner thighs, or penis. Shingles (herpes zoster) usually occurs only once in a lifetime, appears as a rash (clusters of blisters with a red base). Shingles is caused by the same virus that is responsible for chickenpox. Warts are a common, benign skin tumor caused by viral infection.

Anti-inflammatory and Antiallergic Agents

The active agent can be an anti-inflammatory or antiallergic agent. Exemplary anti-inflammatory or antiallergic agents include corticosteroids, non-steroidal anti-inflammatory drugs (NSAIDs), anti-histamines, immunosuppressants and any combination thereof at a therapeutically effective concentration.

The anti-inflammatory active agent is a corticosteroid. The corticosteroid can be selected from the group consisting of clobetasol proprionate, halobetasol proprionate, betamethasone diproprionate, betamethasone valerate, fluocinolone acetonide, halcinonide, betamethasone valerate, fluocinolone acetonide, hydrocortisone valerate, triamcinolone acetonide, hydrocortisone and any combination thereof at a therapeutically effective concentration. Since corticosteroid drugs are typically hydrophobic, suitable foam carriers include high levels of a hydrophobic solvent. The hydrophobic solvent facilitates topical distribution and enhances the rate of penetration of any of the corticosteroid drugs.

The composition may include active agents for the treatment of psoriasis. Corticosteroid ointments, greasy preparations containing little or no water, are commonly used for treating psoriasis. Their main disadvantage is in a sticky feeling subsisting for extended periods subsequent to treatment being completed thereby creating a latent inconvenience and possible discomfort to the treatment recipient. In contrast, the foam composition according to one or more embodiments of the present invention containing high levels of an oil (hydrophobic solvent) spreads very easily throughout the afflicted area and absorbs into the skin without leaving any unpleasant sensation or look. Examples of other inflammatory disorders that are treatable by a foamable composition including a steroid as an active agent are atopic dermatitis, seborrhea, seborrheic dermatitis of the face and trunk, seborrheic blepharitis, contact dermatitis, stasis dermatitis (gravitational eczema; varicose eczema), exfoliative dermatitis (erythroderma), lichen simplex chronicus, pityriasis rosea and pemphigus.

Topical antihistaminic preparations currently available include 1% and 2% diphenhydramine (Benadryl® and Caladryl®), 5% doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines, can also be used.

Polyunsaturated fatty acids containing omega-3 and omega-6 fatty acids (e.g., linoleic and linolenic acid, gamma-linoleic acid (GLA), eicosapentaenoic acid (EPA) and docosahexaenoic acid (DHA) also are beneficial in the treatment of psoriasis and other skin inflammation conditions and may be included in the foamable composition.

Nonsteroidal anti-inflammatory agents (NSAIDs) are useful against skin and systemic bio-abnormalities and can be added to the foam composition. The variety of compounds encompassed by NSAIDs is well-known to those skilled in the art. Specific non-steroidal anti-inflammatory agents useful in the composition include, but are not limited to oxicams, such as piroxicam, isoxicam, tenoxicam, sudoxicam; salicylates, such as salicylic acid, ethyl salicylate, methyl salycilate, aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Any other steroidal and nonsteroidal compounds having the capacity to prevent, alleviate the symptoms of, treat or cure inflammation processes, may be generally included as anti-inflammatory agents.

The pharmaceutical composition may include an anti-inflammatory and/or an antiallergic agent that reduces the occurrence of pro-inflammatory cytokines or inhibits the effect of pro-inflammatory cytokines.

Mixtures of any anti-inflammatory agents can be used in the composition, as well as the dermatologically acceptable salts, esters, amides, prodrugs and derivatives of these agents.

Topical application of a foam, comprising a safe and effective dose of an NSAID can be useful in the prevention and/or alleviation of the symptoms of rheumatoid arthritis, osteoarthritis and pain. Topical NSAIDs, incorporated in the foam composition can be also used in the treatment of dermatological disorders such as acne, rosacea, hair growth disorders, actinic keratosis and certain skin cancer conditions.

Local Anesthetics

The foam compositions may include an effective amount of a topical anesthetic. The topical anesthetic can be selected from the group consisting of benzocaine, lidocaine, bupivacaine, chlorprocaine, dibucaine, etidocaine, mepivacaine, tetracaine, dyclonine, hexylcaine, procaine, cocaine, ketamine, pramoxine, phenol, any pharmaceutically acceptable salts thereof and mixtures of such anesthetic agents. Any mixture of synergistically beneficial anesthetic agents is contemplated Keratolytically Active Agents A keratolytic agent may be included as an active agent of a foamable composition. The term "keratolytically active agent" as used herein includes a compound that loosens and removes the stratum corneum of the skin, or alters the structure of the keratin layers of skin. Keratolytically active agents are used in the treatment of dermatological disorders that involve dry skin, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the treatment of dermatological disorders. Dihydroxybenzene and derivatives thereof have been recognized as potent keratolytic agents. Resorcinol (m-dihydroxybenzene) and derivatives thereof are used in anti-acne preparations. In addition to hydroquinone (p-dihydroxybenzene) having anti-pigmentation properties, hydroquinone is also known to be keratolytic. These compounds also exhibit antiseptic properties. Cresols also possess bactericidal and keratolytic properties.

Vitamin A and vitamin A derivatives, also termed herein "retinoids", such as retinoic acid, isoretinoic acid, retinol and retinal are another class of keratolytically active agents.

Another group of keratolytically active agents include alpha-hydroxy acids, such as lactic acid and glycolic acid and their respective salts and derivatives; and beta-hydroxy acids, such as salicylic acid (o-hydroxybenzoic acid) and salicylic acid salts and pharmaceutically acceptable derivatives.

Another Class of Keratolytically Active Agents Includes Urea and Urea Derivatives. Retinoids Another group of active agents includes retinol, retinal, all trans retinoic acid and derivatives, isomers and analogs thereof, collectively termed "retinoids". Etretinate, actiretin, isotretinoin, adapalene and tazarotene are further examples of said retinoid isomers and analogs. Foamable compositions containing retinoids as the active drug can be used for the treatment of acne, seborrhea, various dermatoses, inflammation of the skin, mucosal membranes, vagina and the rectum, psoriasis, actinic keratosis and skin cancers, by application onto the affected area.

Insecticide and Insect Repellents Agents

Insects such as mosquitoes, biting flies, mites, gnats, fleas, chiggers, punkies, sand flies, lice and ticks can be annoying and sometimes pose a serious risk to human and animal health. In certain areas of the United States, mosquitoes can transmit diseases like equine and St. Louis encephalitis. Biting flies can inflict a painful bite that can persist for days, swell, and become infected. Ticks can transmit serious diseases like Lyme disease and Rocky Mountain spotted fever.

Insect repellents may be added to the foamable composition to protect people and animals from flying or biting insects, spiders, ticks and mites.

Examples of insect repellants include, but are not limited to, DEET (N,N-diethyl-m-toluamide), dimethyl phthalate, piperonyl butoxide and permethrin. Insect repelling terpenoids, have been reported by Hwang, et al, J. Chem. Ecol., 11, 1297 (1985); and Ruledge, J. Am. Mosquito Control Assoc. 4, 414 (1988).

A particular group of insect repellents includes the terpenoid compounds, described in U.S. Pat. No. 5,411,992, including:

(1) Terpenoid-alcohol or terpene-ols are terpenoids which have at least one hydroxyl group. Examples of terpene-ols include: C10H16O compounds, perillyl alcohol, carveol, myrtenol, and cis-verbenol; C10H18O compounds, myrtanol, iso-pinocampheol, dihydrocarveol, isopulegol, terpineol, terpinen-4-ol, nerol, geraniol, and linalool, and C10H20O compounds, menthol, beta-citronellol, and dihydro-myrcenol.

(2) Terpenoid-esters are terpenoids, which have at least one ester group which is the product of the bonding of the hydroxyl group of a terpene-ol with an aliphatic carboxylic acid that can contain functional groups such as the hydroxyl or amine on the aliphatic chain. Examples of suitable aliphatic carboxylic acids include acetic acid, propionic acid, lactic acid, and various amino acids. Examples of terpenoid-esters include: carvyl acetate, carvyl propionate, and menthyl lactate.

(3) Essential oils which contain terpenoids and perfumes which contain terpenoids. Non-limiting examples of essential oils having a high content of terpene-ols and esters include bergamot (62% terpenoids); sage (>50% terpenoids); styrax (>50% terpenoids); peppermint (>50% terpenoids); and pine Siberian (75% terpenoids %). Terpenes, aldehydes and ketones vary in their usefulness but as a general group have potential as insect-repellent.

The foamable composition is particularly suitable for the effective uniform spreading of an insect repellent agent onto large areas of the skin of humans and animals. The hydrophobic solvent present in the foam composition helps retain the insect repellent on the skin surface for an extended period of time.

The foamable composition is suitable for delivery of insect-killing agents (insecticides) to an afflicted external surface area of humans and animals. Thus, the pharmaceutical or cosmetic composition includes an insecticide selected from the group consisting of permethrin, hexachlorobenzene, carbamate, naturally occurring pyrethroids, permethrin, allethrin, malathion, piperonyl butoxide and any combination thereof at a therapeutically effective concentration. The application of the composition is very convenient and it spreads easily, even over hairy areas. The hydrophobic solvent present in the foam composition helps retain the insecticide on the treated area for an extended period of time. Furthermore, the presence of a hydrophobic solvent in the foam eases mechanical removal of lice and nits with a comb.

Anti-cancer Drugs

Anti-cancer drugs can also be used as the drug of choice for the treatment of skin malignant tumors such as basal cell carcinoma, squamous sell carcinoma, melanoma and Kaposi's sarcoma, as well as the pre-cancerous condition actinic keratosis. In certain cases, topical cytotoxic and antiproliferative drugs are used to treat or prevent such cancers, including 5-fluorouracil, also called 5-FU. 5-FU, as well as any other anti-cancer agents, know in the art of cancer medicine, can be incorporated in the foam at therapeutically effective levels. An exemplary family of anticancer drugs, suitable for usage in the foam of the present formulation comprises antiestrogens, such as tamoxifen.

Photodynamic Therapy Agents

The foam composition is also useful to deliver photo-sensitizing agents. A photosensitizer can be selected from the group consisting of poephyrins, modified porphyrins, psoralen, 8-methoxypsoralen, 5-methoxypsoralen, psoralen derivatives, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives and photosensitizer precursors, such as aminolevulinic acid (ALA).

Active Agents for Burns, Wounds, Cuts and Ulcers

The treatment of burns, wounds, cuts and ulcers using a foamable composition is particularly advantageous. The foam can include both anti-infective agents (against bacteria, fungi and/or viruses), antiinflammatory agents (steroidal and/or NSAIDs) and pain relieving components. Upon application, the foam spreads easily, covering the surface of the affected area, and without causing pain.

Skin Care Active Agents

The foam composition is useful and advantageous for skin care and cosmetic care. The combination of oil and water having moisture-retaining properties in a spreadable foam form can be used to substitute currently used cosmetic skin care creams, lotions, gels, etc. The cosmetic foam compositions are suitable for the further application as "cosmeceutical" preparation (cosmetic products with therapeutic benefit), to treat "cosmetic" skin disorders, such as aging skin, wrinkles, hyperpigmentation (melasma, chloasma, freckles, etc.), scaly skin and other skin undesirable properties.

The CTFA Cosmetic Ingredient Handbook describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and humectants facilitating regulating the residence of an active agent in the skin), skin soothing and/or healing agents (e.g., panthenol and derivatives (e.g., ethyl panthenol), aloe vera, pantothenic acid and pantothenic acid derivatives, allantoin, bisabolol, and dipotassium glycyrrhizinate), skin treating agents, thickeners, and vitamins and derivatives thereof.

Anti-acne Active Agents

An anti-acne agent can be included in the foamable composition. The anti-acne agent can be selected from the group consisting of resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, zinc salts and complexes, and combinations thereof, in a therapeutically effective concentration.

Anti-wrinkle Active Agents/Anti-atrophy Active Agents and Agents to Treat Dry and Scaly Skin (Xerosis and Ichthyosis)

The foamable composition may also include an effective amount of an anti-wrinkle active and/or at least one anti-atrophy active. Exemplary anti-wrinkle/anti-atrophy active agents suitable for use in the foamable compositions include sulfur-containing D and L amino acids and their derivatives and salts, particularly the N-acetyl derivatives; thiols; hydroxy acids (e.g., alpha-hydroxy acids such as lactic acid and glycolic acid and their derivatives and salts; or beta-hydroxy acids such as salicylic acid and salicylic acid salts and derivatives), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate). In the case of dry, scaly skin (xerosis) and ichthyosis such agents can alleviate the symptoms by temporary relief of itching associated with these conditions.

Anti-oxidants/Radical Scavengers

An effective amount of an anti-oxidant/radical scavenger can be added to the foamable compositions, for example, in an amount from about 0.1% to about 10% (w/w), or from about 1% to about 5% (w/w).

Anti-oxidants/radical scavengers such as ascorbic acid (vitamin C) and ascorbic acid salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox.®), gallic acid and gallic acid alkyl esters, especially propyl gallate, uric acid and uric acid salts and alkyl esters, sorbic acid and sorbic acid salts, lipoic acid, amines (e.g., N,N-diethylhydroxylamine, amino-guanidine), sulfhydryl compounds (e.g., glutathione), dihydroxy fumaric acid and dihydroxy fumaric acid salts, lysine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts can be used.

The foam is suitable for delivering skin protecting and revitalizing anti-oxidants/radical scavengers. Polyunsaturated fatty acids containing omega-3 and omega-6 fatty acids (e.g., linoleic and linolenic acid, gamma-linoleic acid (GLA), eicosapentaenoic acid (EPA) and docosahexaenoic acid (DHA)) are beneficial in the treatment of psoriasis and other skin inflammation conditions. Likewise, emollients and silicone oils exert moisture-retaining and skin protective effects on the skin. Thus, a skin protective foam is provided, wherein the hydrophobic solvent comprises in full or in part, a solvent, selected from the group of emollients, silicone oil and oils, rich in unsaturated fatty acids, thus, affording a synergistic therapeutic effect of the anti-oxidants/radical scavenger agent and the vehicle components.

Self-tanning Active Agents

The foam composition is particularly suitable for the uniform delivery of a tanning active agent onto large areas of the skin. The compositions contain from about 0.1% to about 20%, or from about 2% to about 7%, or even from about 3% to about 6% of dihydroxyacetone or any other compound know in the art as an artificial tanning active agent.

Skin Lightening and Whitening Agents

The foam composition may be formulated to provide a composition for the uniform delivery of a skin lightening agent. When used, the composition contains from about 0.1% to about 10%, or from about 0.2% to about 5% of a skin-lightening agent. Suitable skin lightening or whitening agents include those known in the art, including hydroquinone, azelaic acid and other related dicarboxylic acids, and salts and derivatives thereof, retinoids, kojic acid, arbutin, nicotinic acid and nicotinic acid precursors, salts and derivatives, ascorbic acid and salts and derivatives thereof (e.g., magnesium ascorbyl phosphate or sodium ascorbyl phosphate), and herbal extracts (e.g., mulberry extract, placental extract).

In one or more embodiments of the present invention, the foam composition includes a combination of at least one skin-whitening agent and at least one additional active agent selected from retinoids, keratolytically active agents and anti-inflammatory agents.

In one or more embodiments, the composition includes a combination of at least one skin-whitening agent and at least one keratolytically active agent selected from a alpha-hydroxy acids, beta hydroxy acids, and retinoids.

In one or more embodiments of the present invention, the foam composition includes a combination of a skin-whitening agent and an inorganic sunscreen agent. When inorganic sunscreen agents, e.g. titanium dioxide and zinc oxide, are rubbed onto the skin, they leave a white coating, which provides an instant (although transient) whitening effect, which is highly desirable by the consumer, who wishes to see instant change in his/her appearance. The whitening agent, in combination with the inorganic sunscreen agent in the foam carrier can be easily and uniformly distributed on the skin surface, thereby affording an even instant whitening effect, unlike creams that are difficult to spread evenly on skin areas.

Agents for Hair Growth Disorders

[Agents that affect the pattern of hair growth can be suitably incorporated in the foam composition. Male pattern baldness (MPB), the commonest cause of balding, is induced by the activity of the male hormone dihydrotestosterone (DHT), which is converted from the hormone testosterone by the enzymes 5-alpha reductase. Current treatments of MPB include minoxidil and agents, which inhibit 5-alpha reductase, such as finasteride, spironolactone, azelaic acid and azelaic acid derivatives and salts. Such agents, as well as other agents known in the art, can be incorporated in the foam composition.

Polyunsaturated fatty acids, i.e., such which include any of the essential fatty acids (EFA's), such as linoleic and linolenic acid, gamma-linoleic acid (GLA), eicosapentaenoic acid (EPA) and docosahexaenoic acid (DHA), are also known to contribute to hair growth. Thus, a hair growth foam composition is provided, in which the hydrophobic solvent comprises in full or in part, an oil, rich in such unsaturated fatty acids.

Figure-forming Agents; Agents to Treat Cellulite/Slimming

Figure forming agents such as used in the treatment of cellulite and in slimming products can be suitably incorporated in the foam composition. A non-limiting exemplary list of active agents known in the treatment of cellulite and in the induction of a slimming effect include:

Herbal extracts: baldderwack extract, butcher's, broom, cayenne, dandelion, red clover, ginkgo biloba, horse chestnut, witch hazel and borage oil Omega 3 and omega 6 oils Caffeic acid and salts and derivatives thereof.

Xanthine agents, such as theophiline and pentoxyphilline

Nicotinic acid and salts and derivatives thereof.

Agents to Treat Sunburn, Heat Burn, Radiation Burn, Rash and Itch

Cosmetic and pharmaceutical ingredients which are known in the art of pharmacology and cosmetology to treat dermatitis, minor skin irritations, sunburn, heat burn, radiation burn, and inhibit inflammation can be beneficially incorporated in the foam composition.

Examples of such active agents include chamomile extract (*matricaria recutitia*), cucumber distillate (*cucumis sativus*), lavender water (*lavendula angustifolia*), rose water (*rosa damascena*), witch hazel (*hamamelis virginiana*), allantoin, bisabolol, rosehip oil, calendula oil, azulaene, menthol and camphor.

Other Skin Care Active Agents

The active agent can be selected from the group of sulfur-containing amino acids, thiol compounds, alpha hydroxy acids, lactic acid and lactic acid derivatives and salts, glycolic acid, glycolic acid derivatives and glycolic acid salts, beta-hydroxy acids, salicylic acid and salicylic acid salts and derivatives, phytic acid, lipoic acid, lysophosphatidic acid, skin peel agents, phenol, resorcinol, vitamin B3 compounds, niacinamide, nicotinic acid and nicotinic acid salts and esters, tocopheryl nicotinate, nicotinyl amino acids, nicotinyl alcohol esters of carboxylic acids, nicotinic acid N-oxide and niacinamide N-oxide, retinoids, retinol, retinal, retinoic acid, retinyl acetate, retinyl palmitate and retinyl ascorbate, caffeine, theophilline, pentoxyphilline, dihydroxy acetone kojic acid, arbutin, nicotinic acid and nicotinic acid precursors, nicotinic acid salts, nicotinic acid derivatives, ascorbic acid, ascorbic acid salts and ascorbic acid derivatives "Alcohol Free"

The foam carrier or foam composition is essentially free of short chain aliphatic alcohols (i.e., methyl, ethyl, isopropyl and butyl alcohol), unlike the composition disclosed in U.S. Pat. Nos. 6,126,920 and 6,358,541, which contains an aliphatic alcohol, preferably in amounts of 40-90% aliphatic alcohol. For the purpose of the present application, the term "alcohol free" refers to compositions that contain no more than 7.5% by weight of any aliphatic alcohol, having one to six carbon atoms in their carbon backbone, or no more than 7.5% by weight of any mixture of such aliphatic alcohols.

Optional Ingredients

The pharmaceutical or cosmetic foam carrier optionally includes a variety of pharmaceutical or cosmetic ingredients, which are added in order to fine-tune the consistency of the formulation, protect the formulation components from degradation and oxidation and bestow their cosmetic acceptability. Such an excipient is preferably selected from the group consisting of: a diglyceride, a triglyceride, a stabilizing agent, an antioxidant, glycerol, a flavoring, a colorant, an odorant agent and any other formulation component known in the art of pharmaceutical and cosmetic formulary. A pharmaceutical or cosmetic composition manufactured using the foam carrier according to the present invention is very easy to use. When applied onto the afflicted body surface of humans or animals, it is in a foam state, allowing free application without spillage. Upon further application of a mechanical force, e.g., by rubbing the composition onto the body surface, it freely spreads on the surface and is rapidly absorbed.

Composition and Foam Physical Characteristics

A pharmaceutical or cosmetic composition manufactured using the foam carrier according to one or more embodiments of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foam composition or carrier includes water, hydrophobic solvents, surfactant, gelling agent and propellant, thereby creating a stable emulsion having an acceptable shelf-life of at least one year, or at least two years at ambient temperature. A feature of a product for cosmetic or medical use is long term stability. Propellants, which are a mixture of low molecular weight hydrocarbons, tend to impair the stability of emulsions. It has been observed, however, that foam compositions including amphiphilic copolymers as gelling agents are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing semi-solid hydrophobic solvents, e.g., white petrolatum, as the main ingredients of the oil phase of the emulsion, exhibit high viscosity and poor flowability and are inappropriate candidates for a foamable composition.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administratable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

A further aspect of the foam is breakability. The breakable foam is thermally stable, yet breaks under sheer force. Sheer-force breakability of the foam is clearly advantageous over thermally-induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of between about 0.01 g/mL and about 0.1 g/mL.

Further Technical Parameters

The composition of the present invention can be contained in and dispensed from a container capable of withstanding the pressure of the propellant gas and having an appropriate valve/nozzle for dispensing the composition as foam under pressure. A customary liquefied propellant can be added, in the amount of about 3-18% of the total composition. Liquefied propellants are gases that exist as liquids under pressure, including high purity hydrocarbons such as propane, isobutane and n-butane, dimethyl ether and chlorofluorocarbons (CFCs).

A specific embodiment according to the present invention comprises placing the composition of the present invention on a patch, regulating residence of an active ingredient in the skin tape or the skin-contact compartment of a transdermal delivery apparatus and applying such object onto the skin, in order to attain effective superficial treatment or enhanced penetration of the drug into the skin or through the skin.

Utilizing such strategy, one can apply drugs, which are currently administered systemically or that require transdermal delivery, in the preferred therapeutic system of the present invention. Examples for such drugs are nicotine, testosterone and other male hormones and male hormone precursors, estrogen and other female hormones and hormone precursors, growth hormone, insulin, caffeine, steroidal and non-steroidal antiinflammatory agents and thyroid hormone substitutes.

The general process, as typically exemplified in Example 1 can be applied in order to produce the composition of the present invention.

The pharmaceutical carrier according to the present invention can also be used to prepare cosmetics for beauty purpose by adding into skin care agents and perfume.

Fields of Pharmaceutical Applications

By including an appropriate active component and optionally an appropriate at least one active agent, the foam composition of the present invention is useful in the therapy of a variety of disorders, such as classified, in a non-limiting exemplary manner, according to the following groups:

Dermatitis including contact dermatitis, atopic dermatitis, seborrheic dermatitis, nummular dermatitis, chronic dermatitis of the hands and feet, generalized exfoliative dermatitis, stasis dermatitis; lichen simplex chronicus; diaper rash; bacterial infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma; fungal infections including dermatophyte infections, yeast infections; parasitic infections including scabies, pediculosis, creeping eruption; viral infections; disorders of hair follicles and sebaceous glands including acne, rosacea, perioral dermatitis, hypertrichosis (hirsutism), alopecia, including male pattern baldness, alopecia greata, alopecia universalis and alopecia totalis; pseudofolliculitis barbae, keratinous cyst; scaling papular diseases including psoriasis, pityriasis rosea, lichen planus, pityriasis rubra pilaris; benign tumors including moles, dysplastic nevi, skin tags, lipomas, angiomas, pyogenic granuloma, seborrheic keratoses, dermatofibroma, keratoacanthoma, keloid; malignant tumors including basal cell carcinoma, squamous cell carcinoma, malignant melanoma, paget's disease of the nipples, Kaposi's sarcoma; reactions to sunlight including sunburn, chronic effects of sunlight, photosensitivity; bullous diseases including pemphigus, bullous pemphigoid, dermatitis herpetiformis, linear immunoglobulin A disease; pigmentation disorders including hypopigmentation such as vitiligo, albinism and postinflammatory hypopigmentation and hyperpigmentation such as melasma (chloasma), drug-induced hyperpigmentation, postinflammatory hyperpigmentation; disorders of cornification including ichthyosis, keratosis pilaris, calluses and corns, actinic keratosis; pressure sores; disorders of sweating; inflammatory reactions including drug eruptions, toxic epidermal necrolysis; erythema multiforme, erythema nodosum, granuloma annulare.

The foam composition is useful in the therapy of non-dermatological disorders, which respond to topical/transdermal delivery of an active agent. By way of example, such disorders include localized pain in general, as well as joint pain, muscle pain, back pain, rheumatic pain, arthritis, ostheoarthritis and acute soft tissue injuries and sports injuries. Other disorders of this class include conditions, which respond to hormone therapy, such as hormone replacement therapy, transdermal nicotine administration, and other respective disorders, known in the art of drug delivery.

The foam compositions are further useful for the treatment and prevention of disorders and diseases of other body cavities including the rectum, vagina, penile urethra and ear canal.

Thus, the foam compositions are useful in treating a patient having any one of a variety of gynecological disorders, such as classified, in a non-limiting exemplary manner, according to the following groups: pelvic pain, including premenstrual syndrome (PMS), mittelschmerz (severe midcycle pain due to ovulation), dysmenorrhea (pain related to the menstrual cycle), endometriosis, ectopic pregnancy, ovarian cysts and masses, acute pelvic inflammatory disease, pelvic congestion syndrome and vulvodynia; vulvovaginal infections, including bacterial vaginosis, candidal vaginitis, trichomonas vaginalis, herpes simplex genital ulcers and warts, pelvic inflammatory disease (PID), cervicitis, acute and chronic salpingitis; endometriosis; gynecological neoplasms, including endometrial Cancer, ovarian cancer, cervical cancer, vulvar cancer, vaginal cancer, fallopian tube cancer and gestational trophoblastic disease; benign tumors; sexually transmitted diseases; sexual dysfunction disorders that respond to pharmacological therapy, including sexual arousal disorder, female orgasmic disorder, dyspareunia and vaginismus; and various gynecological disorders that respond to hormonal therapy.

Rectal applications include, for example, anal abscess/fistula, anal cancer, anal warts, Crohn's disease, haemorrhoids, anal and perianal pruritus, soreness, and excoriation, perianal thrush, anal fissures, fecal incontinence, constipation, polyps of the colon and rectum.

The foam compositions are further useful for intra-vaginal and rectal treatment of sexually-transmitted and non-sexually-transmitted infectious disease (STDs).

In one or more embodiments, the invention provides a method of treatment of a disorder of the skin, mucosal membrane, ear channel, vaginal, rectal and penile urethra disorders, comprising topical application of the foam composition, whereby one or more active agents, in a therapeutically effective concentration to the afflicted area.

In a further embodiment, the invention provides a method of treatment of a non-dermatological disorder, which responds to topical delivery of an active agent, comprising topical application of the foam composition of the present invention, whereby one or more active agents, in a therapeutically effective concentration to the skin.

Treatment/Therapy

The terms "therapy" and "treatment" as used herein interchangeably, cover any treatment of a disease or disorder, and includes, for example:
 (i) Curing the disease or disorder;
 (ii) preventing the disease or disorder from occurring in a subject which may be predisposed to the disease but has not yet been diagnosed as having it;
 (iii) inhibiting the disease or disorder;
 (iv) relieving the disease or disorder;
 (v) causing regression of the disease;

(vi) providing a beneficial immunological effect;
(vii) improving the quality of life of a subject afflicted by a disease or disorder; and, in the case of cosmetic treatment
(viii) cleansing, beautifying, promoting attractiveness, or altering the appearance without affecting the body's structure or functions

EXAMPLES

In the following, we are going to describe some examples and experiments in detail. This invention is not limited to these examples and experiments. Many variations will suggest themselves are within the full intended scope of the appended claims.

Example 1

Production of Pharmaceutical or Cosmetic Foam Carrier and Composition—General Method The method for preparing of a pharmaceutical foam carrier generally comprised following steps.

Step 1—Aqueous Phase: Gelling agent and surface-active agent are dissolved in water, with agitation. The solution is warmed to 50-70° C. Water soluble cosmetic or pharmaceutical active Ingredients* and optional water soluble ingredients are added with agitation to the Aqueous Phase mixture.

Step 2—Hydrophobic Phase: The hydrophobic solvent is heated to same temperature. Oil soluble cosmetic or pharmaceutical active agents* and optional oil soluble formulation ingredients are added with agitation to the Hydrophobic Phase mixture.

Step 3—The warm Hydrophobic Phase is gradually poured into the warm Aqueous Phase, with agitation, followed by Ultraturax homogenization. The mixture is allowed to cool down to ambient temperature.

Step 4—The mixture, at ambient temperature, is added to an aerosol container, the container is sealed and appropriate amount of propellant (about 10% of the composition mass) is compressed into the container.

* In case of heat sensitive active ingredients, add the active ingredient with agitation to the mixture, after Step 3.

In the following examples, foam compositions were prepared as described above and tested for foam quality Example 2

Diclofenac Foam Composition with Transcutol

| Component | % w/w |
|---|---|
| Mineral oil (hydrophobic solvent) | 6.00 |
| Isopropyl myristate (hydrophobic solvent) | 6.00 |
| Stearyl alcohol (foam adjuvant) | 1.00 |
| Xanthan gum (gelling agent) | 0.30 |
| Methocel K100M (gelling agent) | 0.30 |
| TWEEN 80 (surfactant) | 1.00 |
| MYRJ 49p (surfactant) | 3.00 |
| Cocamidopropyl betaine (surfactant) | 0.50 |
| Transcutol p (therapeutic enhancer) | 20.00 |
| Glyceryl monostearate (co-emulsifier) | 0.50 |
| Diclofenac sodium (active agent) | 1.00 |
| Phenonip (preservative) | 0.30 |
| Butane/propane (propellant) | 8.00 |
| Water | to 100.0 |
| Foam Quality | E |
| Density | 0.028 |

Example 3

Local Anesthetic Lidocaine Foam Compositions with Either Urea, Lactic Acid or a Therapeutic Enhancer

| Component | % w/w | | | | |
|---|---|---|---|---|---|
| Mineral oil | 6.00 | 6.00 | 6.00 | 6.00 | 12.00 |
| Isopropyl myristate | 6.00 | 6.00 | 6.00 | 6.00 | 12.00 |
| Glyceryl monostearate | 0.50 | 0.50 | 0.50 | 0.50 | 1.00 |
| Stearyl alcohol | 1.00 | 1.00 | 1.00 | 1.00 | 1.00 |
| Xanthan gum | 0.30 | 0.30 | 0.30 | 0.30 | 0.30 |
| Methocel K100M | 0.30 | 0.30 | 0.30 | 0.30 | 0.30 |
| TWEEN 60 | 1.00 | | | | |
| TWEEN 80 | | 1.00 | 1.00 | 1.00 | 2.00 |
| MYRJ 49p | 3.00 | 3.00 | 3.00 | 3.00 | 4.00 |
| Lactic acid | 10.00 | 5.00 | | | |
| Glycofurol | | | 1.00 | 10.00 | |
| Urea | | | | | 10.00 |
| Cocamidopropyl betaine | — | 0.50 | — | 0.50 | — |
| Lidocaine base | 4.00 | 4.00 | 4.00 | 4.00 | 4.00 |
| Phenonip | 0.30 | 0.30 | 0.30 | 0.30 | 0.30 |
| Butane/propane | 8 | 8 | 6 | 10 | 10 |
| Water | to 100 | to 100 | to 100 | to 100 | to 100 |
| Foam Quality | E | E | E | E | E |
| Density | 0.028 | 0.038 | 0.044 | 0.028 | 0.028 |
| Mineral oil | 6.00 | 6.00 | 6.00 | 22.00 | 6.00 |
| Isopropyl myristate | 6.00 | 6.00 | 6.00 | 22.00 | 6.00 |
| Glyceryl monostearate | 0.50 | 0.50 | 0.50 | 1.00 | 0.50 |
| Stearyl alcohol | 1.00 | 1.00 | 1.00 | 1.00 | 1.00 |
| Xanthan gum | 0.30 | 0.30 | 0.30 | 0.40 | 0.30 |
| Methocel K100M | 0.30 | 0.30 | 0.30 | 0.40 | 0.30 |
| TWEEN 80 | | 1.00 | 1.00 | 2.00 | 1.00 |
| MYRJ 49p | 1.00 | 3.00 | 3.00 | 4.00 | 3.00 |
| Propylene glycol | 3.00 | | | | |
| Transcutol p | | 10.00 | 1.00 | 2.00 | 10.00 |
| Cocamidopropyl betaine | 0.50 | 0.50 | 0.50 | 0.50 | 0.50 |
| Lidocaine base | 4.00 | 4.00 | 4.00 | 4.00 | 4.00 |
| Phenonip | 0.30 | 0.30 | 0.30 | 0.30 | 0.30 |
| Butane/propane | 8 | 8 | 6 | 8 | 10 |
| Water | to 100 | to 100 | to 100 | to 100 | to 100 |
| Foam Quality | E | E | E | E | E |
| Density | 0.032 | 0.035 | 0.048 | 0.075 | 0.025 |

Example 4

Foam Compositions with Urea

| Component | % w/w | | | |
|---|---|---|---|---|
| Mineral oil | 6.00 | 6.00 | 6.00 | 6.00 |
| Isopropyl myristate | 6.00 | 6.00 | 6.00 | 6.00 |
| Glyceryl monostearate | 0.50 | 0.50 | 0.50 | 0.50 |
| Stearyl alcohol | 0.20 | 0.20 | 0.20 | 1.00 |
| Urea | 10.00 | 10.00 | 10.00 | 10.00 |
| Xanthan gum | 0.30 | 0.30 | 0.30 | 0.30 |
| Methocel K100M | 0.30 | 0.30 | 0.30 | 0.30 |
| Myrj 52 | | | | 3.00 |
| TWEEN 80 | | | | 1.00 |
| Myrj 49p | | | | 3.00 |

-continued

| Component | | | | |
|---|---|---|---|---|
| TWEEN 60 | 1.00 | 1.00 | 1.00 | |
| Cocamidopropyl betaine | 0.50 | 0.50 | 0.50 | |
| Phenonip | 0.30 | 0.30 | 0.30 | 0.30 |
| Butane/propane | 8.00 | 8.00 | 8.00 | 6.00 |
| Water | to 100 | to 100 | to 100 | to 100 |
| Foam Quality | E | E | E | E |
| Density | n/a | 0.023 | n/a | 0.044 |
| Mineral oil | 6.00 | | 6.00 | |
| Isopropyl myristate | 6.00 | | 6.00 | |
| Glyceryl monostearate | 0.50 | | 0.50 | |
| Stearyl alcohol | 1.00 | | 1.00 | |
| Urea | 40.00 | 40.00 | 20.00 | 20.00 |
| Xanthan gum | 0.30 | 0.30 | 0.30 | 0.30 |
| Methocel K100M | 0.30 | 0.30 | 0.30 | 0.30 |
| Myrj 52 | 3.00 | 3.00 | 3.00 | 3.00 |
| TWEEN 80 | 1.00 | 1.00 | 1.00 | 1.00 |
| Cocamidopropyl betaine | 0.50 | 0.50 | | 0.50 |
| Phenonip | 0.30 | 0.30 | 0.30 | 0.30 |
| Butane/propane | 8.00 | 6.00 | 8.00 | 8.00 |
| Water | to 100 | to 100 | to 100 | to 100 |
| Foam Quality | E | E | E | E |
| Density | 0.022 | 0.029 | 0.032 | 0.024 |

| Component | % w/w |
|---|---|
| Capric/caprylic triglycerides | 12.00 |
| Glyceryl monostearate | 0.50 |
| Tween 80 | 3.0 |
| Pemulene TR1 | 0.50 |
| Hydrophilic Drug | 1.0 |
| Urea | 10.0 |
| Phenonip | 0.30 |
| Butane/propane | 8.00 |
| Water | to 100 |
| Foam Quality | E |
| Density | 0.030 |
| Capric/caprylic triglycerides | 12.00 |
| Glyceryl monostearate | 0.50 |
| Tween 80 | 3.0 |
| Pemulene TR1 | 0.50 |
| Hydrophobic Drug | 1.0 |
| Urea | 10.0 |
| Phenonip | 0.30 |
| Butane/propane | 8.00 |
| Water | to 100 |
| Foam Quality | E |
| Density | 0.030 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Urea | 10.00 |
| Cocamidopropyl betaine | 0.50 |
| Hydrophilic Drug | 0.1-2.0 |
| Phenonip | 0.30 |
| Butane/propane | 6.00 |
| Water | to 100 |
| Foam Quality | E |
| Density | 0.034 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Urea | 10.00 |
| Cocamidopropyl betaine | 0.50 |
| Lipophilic Drug | 2.0 |
| Phenonip | 0.30 |
| Butane/propane | 8.00 |
| Water | to 100 |
| Foam Quality | E |
| Density | 0.020 |
| Capric/caprylic triglycerides | 12.00 |
| Glyceryl monostearate | 0.50 |
| Pemulene TR1 | 0.50 |

-continued

| Component | % w/w |
|---|---|
| Methocel K100M | 0.30 |
| Xanthan gum | 0.30 |
| Urea | 10.00 |
| Ketoconazole | 1.0 |
| Phenonip | 0.30 |
| Butane/propane | 8.00 |
| Water | to 100 |
| Foam Quality | E |
| Density | 0.020 |

Example 5

Further Foam Composition with Either Transcutol or Glycofurol

| Component | % w/w |
|---|---|
| Isopropyl myristate | 30.00 |
| Glyceryl monostearate | 0.50 |
| Xanthan gum | 0.30 |
| Methocel K100M | 0.30 |
| TWEEN 80 | 1.00 |
| MYRJ 49p | 3.00 |
| Cocamidopropyl betaine | 0.50 |
| Transcutol p | 20.00 |
| Hyrdophylic drug | 1.0 |
| Phenonip | 0.30 |
| Butane/propane | 8.00 |
| Water | to 100 |
| Foam Quality | E |
| Density | 0.028 |
| Isopropyl myristate | 30.00 |
| Glyceryl monostearate | 0.50 |
| Xanthan gum | 0.30 |
| Methocel K100M | 0.30 |
| TWEEN 80 | 1.00 |
| MYRJ 49p | 3.00 |
| Cocamidopropyl betaine | 0.50 |
| Transcutol p | 20.00 |
| Hyrdophobic drug | 1.0 |
| Phenonip | 0.30 |
| Water | to 100 |
| Butane/propane | 8.00 |
| Foam Quality | E |
| Density | 0.030 |
| Capric/caprylic triglycerides | 12.00 |
| Glyceryl monostearate | 0.50 |
| Pemulene TR1 | 0.50 |
| Methocel K100M | 0.30 |
| Xanthan gum | 0.30 |
| Transcutol | 10.00 |
| Ketoconazole | 1.0 |
| Phenonip | 0.30 |
| Water | to 100 |
| Butane/propane | 8.00 |
| Foam Quality | E |
| Density | 0.038 |
| Capric/caprylic triglycerides | 12.00 |
| Glyceryl monostearate | 0.50 |
| Pemulene TR1 | 0.50 |
| Methocel K100M | 0.30 |
| Xanthan gum | 0.30 |
| Glycofurol | 10.00 |
| Ketoconazole | 1.0 |
| Phenonip | 0.30 |
| Water | to 100 |
| Butane/propane | 8.00 |
| Foam Quality | E |
| Density | 0.034 |

Example 6

Foam Compositions with Hydroxy Acids

| Component | % w/w |
|---|---|
| Capric/caprylic triglycerides | 18.00 |
| Glyceryl monostearate | 0.50 |
| Pemulene TR1 | 0.50 |
| Methocel K100M | 0.30 |
| Xanthan gum | 0.30 |
| Hydrophilic Drug | 1.0 |
| Lactic acid | 6.0 |
| Phenonip | 0.30 |
| Butane/propane | 8.00 |
| Water | to 100 |
| Foam Quality | E |
| Density | 0.030 |
| Capric/caprylic triglycerides | 18.00 |
| Glyceryl monostearate | 0.50 |
| Pemulene TR1 | 0.50 |
| Methocel K100M | 0.30 |
| Xanthan gum | 0.30 |
| Hydrophobic Drug | 1.0 |
| Lactic acid | 6.0 |
| Phenonip | 0.30 |
| Butane/propane | 6.00 |
| Water | to 100 |
| Foam Quality | E |
| Density | 0.038 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Glycolic acid | 4.00 |
| Cocamidopropylbetaine | 0.50 |
| Hydrophylic Drug | 2.0 |
| Phenonip | 0.30 |
| Butane/propane | 6.00 |
| Water | to 100 |
| Foam Quality | E |
| Density | 0.044 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Glycolic acid | 4.00 |
| Cocamidopropylbetaine | 0.50 |
| Hydrohobic Drug | 2.0 |
| Phenonip | 0.30 |
| Butane/propane | 12.00 |
| Water | to 100 |
| Foam Quality | E |
| Density | 0.020 |

Although various embodiments that incorporate the teachings of the present invention have been shown and described in detail herein, those skilled in the art can readily devise many other varied embodiments that incorporate these teachings.

What is claimed is:

1. A method of skin or mucosal surface application comprising spreading or collapsing a breakable thermally stable foam by mechanical force at or about a target site of a subject, the breakable thermally stable foam obtained by dispensing a foamable emulsion composition comprising (i) about 0.1 to about 5% by weight of a surface-active agent;
(ii) about 5 to about 50% by weight of a liquid, non-volatile hydrophobic solvent;
(iii) about 0.1 to about 5% by weight of a gelling agent; and
(iv) a component selected from the group consisting of urea, a hydroxy acid, a therapeutic enhancer, and mixtures of two or more thereof;
(v) water; and
(vi) a liquefied or a compressed gas propellant;
wherein the foamable emulsion composition contains no more than 7.5% by weight methyl alcohol, ethyl alcohol, isopropyl alcohol, butyl alcohol, or mixtures thereof.

2. The method of claim 1, wherein the foam has a specific gravity of between about 0.01 g/mL and about 0.1 g/mL.

3. The method of claim 1, wherein the surface-active agent has an HLB in the range of about 9 to 14.

4. The method of claim 1, wherein the surface-active agent is a non-ionic surfactant.

5. The method of claim 1, wherein the gelling agent comprises an amphiphilic copolymer.

6. The method of claim 1, wherein the component consists of about 1% to about 50% by weight of urea.

7. The method of claim 1, wherein the component consists of about 10% to about 20% by weight of urea.

8. The method of claim 1, wherein the component consists of about 20% to about 50% by weight of urea.

9. The method of claim 1, wherein the component consists of about 1% to about 30% by weight of at least one hydroxy acid.

10. The method of claim 1, wherein the component consists of about 1% to about 10% by weight of at least one hydroxy acid.

11. The method of claim 1, wherein the component consists of a combination of about 1% to about 50% by weight of urea and about 1% to about 30% by weight of at least one hydroxy acid.

12. The method of claim 1, wherein the component consists of at about 1% to about 30% by weight of at least one therapeutic enhancer selected from the group consisting of propylene glycol, butylene glycols, glycerol, pentaerythritol, sorbitol, mannitol, oligosaccharides, dimethyl isosorbide, monooleate of ethoxylated glycerides (with 8 to 10 ethylene oxide units), polyethylene glycol 200-600, transcutol (diethylene glycol monoethyl ether), glycofurol (tetrahydrofurfuryl alcohol), PEG ether, and a cyclodextrin.

13. The method of claim 1, wherein the component comprises at least one humectant or moisture-retaining agent.

14. The method of claim 1, wherein the composition further comprises a foam adjuvant.

15. The method of claim 1, wherein the composition further comprises a therapeutically effective concentration of at least one active agent.

16. The method of claim 15, wherein the active agent is at least one agent selected from the group consisting of an antibacterial agent, an anti-fungal agent, an anti-viral agent, an anti-inflammatory agent, a steroid, a corticosteroid, antihistamine, a nonsteroidal anti-inflammatory agent, an immonumodulating agent, an immunosuppressant, an anti-allergic agent, a local anesthetic agent, a keratolytically active agent, a retinoid, an insecticide, an insect repellent, an anticancer drug, a photodynamic therapy agent, an active agents for burns, wounds, cuts and ulcers, an anti-acne active agent, an anti-wrinkle active agent, an anti-atrophy active agent, an anti-oxidant, a radical scavenger, a self-tanning active agent, a skin lightening or whitening agent, an agent suitable for the treatment of a hair growth disorder, a humectant, a moisture-retaining agent, a hydroxy acid, and an agent for treating cellulite.

17. The method of claim 1, wherein the ratio between the surface active agent and the hydrophobic solvent is between about 1:8 and about 1:16.

18. The method of claim 1, wherein the ratio between the surface active agent and the hydrophobic solvent is between about 1:16 and about 1:32.

19. The method of claim 1, wherein the emulsion is an oil in water emulsion.

20. The method of claim 6, wherein the skin or mucosal surface application is for ameliorating a skin or mucosal disorder selected from the group consisting of one or more of pain, wounds, burns, cuts, ulcers, ear channel disorders, vaginal disorders, rectal disorders, penile disorders, and urethra disorders.

21. The method of claim 9, wherein the skin or mucosal surface application is for ameliorating a skin or mucosal disorder selected from the group consisting of one or more of pain, wounds, burns, cuts, ulcers, ear channel disorders, vaginal disorders, rectal disorders, penile disorders, and urethra disorders.

22. The method of claim 15, wherein the skin or mucosal application is for ameliorating a disorder that is known to be responsive to the at least one active agent, wherein the disorder is selected from the group consisting of contact dermatitis, atopic dermatitis, seborrheic dermatitis, nummular dermatitis, chronic dermatitis of the hands or feet, generalized exfoliative dermatitis, stasis dermatitis, diaper rash, bacterial infections, cellulitis, fungal infections, parasitic infections, scabies, pediculosis, viral infections, disorders of hair follicles, disorders of sebaceous glands, acne, rosacea, perioral dermatitis, psoriasis, basal cell carcinoma, squamous cell carcinoma, melanoma reactions to sunlight, sunburn, photosensitivity, bullous diseases, vitiligo, hyperpigmentation, ichthyosis, actinic keratosis, pressure sores, disorders of sweating, non-dermatological disorders which respond to topical or transdermal delivery of an active agent, localized pain, joint pain, muscle pain, back pain, ostheoarthritis, conditions which respond to hormone therapy, pelvic pain, vulvovaginal infections, bacterial vaginosis, candidal vaginitis, trichomonas vaginalis, herpes simplex, genital ulcers, genital warts, sexually transmitted diseases, sexual dysfunction disorders that respond to pharmacological topical therapy, erectile dysfunction, anal fistula, anal warts, haemorrhoids, and anal fissures.

23. A method of skin or mucosal surface application comprising spreading or collapsing a breakable thermally stable foam by mechanical force at or about a target site of a subject, the breakable thermally stable foam obtained by dispensing a foamable emulsion composition comprising:
   about 0.1 to about 5% by weight of a surface-active agent, wherein the surface active agent comprises one or more of a polysorbate, a polyoxyethylene fatty acid ester, a poly(oxyethylene) alkyl ether, a sucrose ester, a partial ester of sorbitol, a sorbitol anhydride, isoceteth-20, sodium methyl cocoyl taurate, sodium methyl oleoyl taurate, sodium lauryl sulfate, triethanolamine lauryl sulfate, a betaine, a mono-, di- or tri-ester of sucrose with food fatty acids (sucrose esters), a monoglyceride, a diglyceride, polyoxyethylene (20) sorbitan monostearate, polyoxyethylene (20) sorbitan monooleate, polyoxyethylene (8) stearate, polyoxyethylene (20) stearate, polyoxyethylene (100) stearate, a polyoxyethylene cetyl ether, a polyoxyethylene palmityl ether, a polyethylene oxide hexadecyl ether, polyoxyethylene (2) cetyl ether, polyoxyethylene (10) cetyl ether, sorbitan monolaurate, isoceteth-20, cocamidopropyl betaine, and polyoxyethylene 40 stearate;
   (ii) about 0.1 to about 5% by weight of a gelling agent;
   (iii) a therapeutic enhancer and a component selected from the group consisting of urea, hydroxyl acid, an active agent, and combinations of two or more thereof;
   (iv) water; and
   (v) a liquefied or a compressed gas propellant;
   wherein the composition contains no more than 7.5% by weight methyl alcohol, ethyl alcohol, isopropyl alcohol, butyl alcohol, or mixtures thereof.

24. The method of claim 15, wherein the skin or mucosal surface application is for ameliorating a disorder selected from the group consisting of one or more of pain, wounds, burns, cuts, ulcers, ear channel disorders, vaginal disorders, rectal disorders, penile disorders, and urethra disorders.

* * * * *

UNITED STATES PATENT AND TRADEMARK OFFICE
CERTIFICATE OF CORRECTION

PATENT NO.        : 8,435,498 B2
APPLICATION NO.   : 12/752718
DATED             : May 7, 2013
INVENTOR(S)       : Dov Tamarkin et al.

It is certified that error appears in the above-identified patent and that said Letters Patent is hereby corrected as shown below:

On the Title Page
Page 1, Column 1 (Related U.S. Application Data), Line 4, please delete "Oct. 24, 2002," and insert -- Oct. 24, 2003, --, therefor.

Page 1, Column 2 (Primary Examiner), Line 1, please delete "Abigal Fisher" and insert -- Abigail Fisher --, therefor.

Page 8, Column 2 (Other Publications), Line 50, please delete "ofdandruff/" and insert -- of dandruff/ --, therefor.

Page 9, Column 1 (Other Publications), Line 21, please delete "phase" and insert -- phase inversion Temperature --, therefor.

Page 9, Column 1 (Other Publications), Line 41, please delete "Invections," and insert -- Infections, --, therefor.

Page 9, Column 1 (Other Publications), Line 43, please delete "surfacants"," and insert -- surfactants", --, therefor.

Page 9, Column 1 (Other Publications), Line 47, please delete "Abstrace," and insert -- Abstract, --, therefor.

Page 9, Column 1 (Other Publications), Line 48, please delete "Revtrieved" and insert -- Retrieved --, therefor.

Page 9, Column 1 (Other Publications), Line 51, please delete "Intraephithelial" and insert -- Intraepithelial --, therefor.

Signed and Sealed this
Eleventh Day of February, 2014

Michelle K. Lee
*Deputy Director of the United States Patent and Trademark Office*

Page 9, Column 1 (Other Publications), Line 53, please delete "Genetial" and insert -- Genital --, therefor.

Page 9, Column 1 (Other Publications), Line 69, please delete "Soulbility" and insert -- "Solubility --, therefor.

Page 9, Column 2 (Other Publications), Line 11, please delete "Immiquimod" and insert -- Imiquimod --, therefor.

Page 9, Column 2 (Other Publications), Line 14, please delete "Micralax" and insert -- Microlax --, therefor.

Page 9, Column 2 (Other Publications), Line 22, please delete "Aracel" and insert -- Arlacel --, therefor.

Page 9, Column 2 (Other Publications), Line 38, please delete "Safey" and insert -- Safety --, therefor.

Page 10, Column 1 (Other Publications), Line 16, please delete "Irriadiation,"" and insert -- Irradiation," --, therefor.

Page 10, Column 1 (Other Publications), Line 18-19, please delete "Gasroenterology," and insert -- Gastroenterology, --, therefor.

Page 10, Column 1 (Other Publications), Line 30, please delete "Antivial" and insert -- Antiviral --, therefor.

Page 10, Column 1 (Other Publications), Line 34, please delete "Iminquimod" and insert -- Imiquimod --, therefor.

Page 10, Column 1 (Other Publications), Line 60, please delete "/Surfacant" and insert -- /Surfactant --, therefor.

Page 10, Column 1 (Other Publications), Line 65, please delete "Effacy" and insert -- Efficacy --, therefor.

Page 10, Column 1 (Other Publications), Line 66, please delete "Sesquichlorhydrate" and insert -- Sesquichlorohydrate --, therefor.

Page 10, Column 2 (Other Publications), Line 27, please delete "Kosmetic" and insert -- Kosmetik --, therefor.

Page 10, Column 2 (Other Publications), Line 32, please delete "clobestasol" and insert -- clobetasol --, therefor.

Page 11, Column 1 (Other Publications), Line 1, please delete "Dictionaary," and insert -- Dictionary, --, therefor.

Page 11, Column 1 (Other Publications), Line 18, please delete "-techology/." and insert -- -technology/. --, therefor.

Page 11, Column 1 (Other Publications), Line 22, please delete ""Opitmization" and insert -- "Optimization --, therefor.

Page 11, Column 1 (Other Publications), Line 34, please delete ""Phospho-olicines" and insert -- "Phospho-olivines --, therefor.

Page 11, Column 1 (Other Publications), Line 37, please delete "Microemulstions" and insert -- Microemulsions --, therefor.

Page 11, Column 2 (Other Publications), Line 51, please delete "Polyvinlpyrrolidone" and insert -- Polyvinylpyrrolidone --, therefor.

Page 12, Column 1 (Other Publications), Line 4, please delete "Minosidil" and insert -- Minoxidil --, therefor.

Page 12, Column 1 (Other Publications), Line 59, please delete "epidermal" and insert -- epidermal permeability --, therefor.

Page 12, Column 1 (Other Publications), Line 64, please delete "Chemothery," and insert -- Chemotherapy, --, therefor.

Page 12, Column 2 (Other Publications), Line 48, please delete "keratinoacytes" and insert -- keratinocytes --, therefor.

Page 12, Column 2 (Other Publications), Line 57, please delete "efects" and insert -- effects --, therefor.

Page 12, Column 2 (Other Publications), Line 60, please delete "biodegrabable" and insert -- biodegradable --, therefor.

Page 12, Column 2 (Other Publications), Line 66, please delete "nffedipine" and insert -- nifedipine --, therefor.

Page 13, Column 2 (Other Publications), Line 7, please delete "providone-" and insert -- povidone- --, therefor.

In the Specifications

Column 3, Line 46, please delete "stain cloths" and insert -- stain clothes --, therefor.

Column 10, Line 57-58, please delete "betamethasone valerate, fluocinolone acetonide", therefor.

Column 12, Line 43, please delete "Retinoids", therefor.

Column 12, Before Line 44, please insert header -- Retinoid --, therefor.

Column 16, Line 36, please remove "[", therefor.

Column 18, Line 52, please remove "sheer force." and insert -- shear force. --, therefor.

Column 18, Line 52-53, please delete "Sheer-force" and insert -- Shear-force --, therefor.

Column 22, between lines 33 (after Density) and 34 (before Mineral oil), please insert the following header --

| Component | % w/w |
|---|---|
| | |

--, therefor.

Column 23, between Lines 8 (after Density) and 9 (after Mineral oil), please insert the following header --

| Component | % w/w |
|---|---|
| | |

--, therefor.

Column 23, between Lines 31 (after Density) and 32 (before Capric/caprylic triglycerides), please insert the following header --

| Component | % w/w |
|---|---|
| | |

--, therefor.

Column 23, between Lines 39 (after Density) and 40 (before Capric/caprylic triglycerides), please insert the following header --

| Component | % w/w |
|---|---|
| | |

--, therefor.

Column 23, between Lines 52 (after Density) and 53 (before Capric/caprylic triglycerides), please insert the following header --

| Component | % w/w |
|---|---|
| | |

--, therefor.

Column 23, between Lines 63 (after Density) and 64 (before Capric/caprylic triglycerides), please insert the following header --

| Component | % w/w |
|---|---|
| | |

--, therefor.

CERTIFICATE OF CORRECTION (continued)
U.S. Pat. No. 8,435,498 B2

Column 24, between Lines 35 (after Density) and 36 (before Isopropyl myristate), please insert the following header -- | Component | % w/w | --, therefor.

Column 24, between Lines 45 (after Density) and 46 (before Capric/caprylic triglycerides), please insert the following header -- | Component | % w/w | --, therefor.

Column 24, between Lines 56 (after Density) and 57 (before Capric/caprylic triglycerides), please insert the following header -- | Component | % w/w | --, therefor.

Column 25, between Lines 18 (after Density) and 19 (before Capric/caprylic triglycerides), please insert the following header -- | Component | % w/w | --, therefor.

Column 25, Lines 28 (after Density) and 29 (Capric/caprylic triglycerides), please insert the following header -- | Component | % w/w | --, therefor.

Column 25, Lines 40 (after Density) and 41 (before Capric/caprylic triglycerides), please insert the following header -- | Component | % w/w | --, therefor.

In the Claims
Column 25 (Claim 1), Line 67, please delete "comprising" and insert -- comprising: --, therefor.

Column 26 (Claim 16), Line 57, please delete "immonumodulating" and insert -- immunomodulating --, therefor.

Column 26 (Claim 16), Line 60, please delete "agents" and insert -- agent --, therefor.

Column 27 (Claim 22), Line 37, please delete "ostheoarthritis," and insert -- osteoarthritis, --, therefor.

Column 28 (Claim 23), Line 9, please delete "about" and insert -- (i) about --, therefor.

Column 28 (Claim 23), Line 25, please delete "isoceteth-20", therefor.

UNITED STATES PATENT AND TRADEMARK OFFICE
CERTIFICATE OF CORRECTION

| | | |
|---|---|---|
| PATENT NO. | : 8,435,498 B2 | Page 1 of 1 |
| APPLICATION NO. | : 12/752718 | |
| DATED | : May 7, 2013 | |
| INVENTOR(S) | : Tamarkin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 129 days.

Signed and Sealed this
Twenty-first Day of October, 2014

Michelle K. Lee
*Deputy Director of the United States Patent and Trademark Office*